US008685439B2

(12) United States Patent
Chapin et al.

(10) Patent No.: US 8,685,439 B2
(45) Date of Patent: Apr. 1, 2014

(54) METHOD FOR THE TREATMENT AND PREVENTION OF EYELID SWELLING

(75) Inventors: Matthew Jonathan Chapin, Amesbury, MA (US); Mark Barry Abelson, Andover, MA (US); Keith Jeffrey Lane, Somerville, MA (US); Akimitsu Makino, Arlington, MA (US)

(73) Assignee: Aciex Therapeutics, Inc., Boston, MA (US)

( * ) Notice: Subject to any disclaimer, the term of this patent is extended or adjusted under 35 U.S.C. 154(b) by 1170 days.

(21) Appl. No.: 11/796,278

(22) Filed: Apr. 26, 2007

(65) Prior Publication Data
US 2007/0264318 A1 Nov. 15, 2007

Related U.S. Application Data

(60) Provisional application No. 60/794,983, filed on Apr. 26, 2006, provisional application No. 60/845,479, filed on Sep. 18, 2006.

(51) Int. Cl.
*A61F 13/02* (2006.01)
(52) U.S. Cl.
USPC .............. 424/448; 424/680; 514/23; 514/53; 514/738
(58) Field of Classification Search
None
See application file for complete search history.

(56) References Cited

U.S. PATENT DOCUMENTS

| | | | |
|---|---|---|---|
| 2,618,428 A | 11/1952 | Harrison | |
| 4,271,143 A | 6/1981 | Schoenwald et al. | 424/78 |
| 4,407,791 A | 10/1983 | Stark | 424/80 |
| 4,407,792 A | 10/1983 | Schoenwald et al. | 424/81 |
| 4,454,151 A | 6/1984 | Waterbury | 424/274 |
| 4,615,697 A | 10/1986 | Robinson | 604/890 |
| 4,933,177 A | 6/1990 | Grollier et al. | 424/74 |
| 4,960,799 A | 10/1990 | Nagy | 514/567 |
| 5,556,848 A | 9/1996 | Kimura et al. | |
| 5,811,446 A | 9/1998 | Thomas | |
| 6,806,364 B2 | 10/2004 | Su et al. | 536/43 |
| 6,964,783 B1 * | 11/2005 | Shrivastava | 424/725 |
| 2002/0061340 A1 * | 5/2002 | Shahinian, Jr. | 424/725 |
| 2005/0059639 A1 * | 3/2005 | Wei | 514/142 |
| 2005/0147679 A1 | 7/2005 | Petito et al. | 424/484 |
| 2006/0057081 A1 | 3/2006 | Boxrud | |
| 2006/0110331 A1 | 5/2006 | Dang et al. | |
| 2008/0051385 A1 | 2/2008 | Parasrampuria et al. | |

FOREIGN PATENT DOCUMENTS

| | | |
|---|---|---|
| DE | 10000612 | 7/2001 |
| EP | 0 517 160 A1 | 12/1992 |
| GB | 2 007 091 A | 5/1979 |
| JP | 2004-123729 | 4/2004 |
| WO | WO 92/00707 | 1/1992 |
| WO | WO 00/37080 | 6/2000 |
| WO | WO-01/54684 A1 | 8/2001 |
| WO | WO 2007/127333 | 11/2007 |

OTHER PUBLICATIONS

Duzman, E., J. Anderson, J.B. Vita, J.C. Lue, C. Chen, and I.H. Leopold. 1983. Topically Applied Oxymetazoline: Ocular Vasoconstrictive Activity, Pharmacokinetics, and Metabolism. Arch Ophthalmol. 101: 1122-1126.*
Abelson, M.B., and K. Fink. 2002. Allergy: How to Treat Lid Swelling. Rev Ophthalmol. 9(8): 8 pages.*
Duzman, E., J. Anderson, J.B. Vita, J.C. Lue, C-C. Chen, and I.H. Leopold. 1983. Topically Applied Oxymetazoline-Ocular Vasoconstrictive Activity, Pharmacokinetics, and Metabolism. Arch. Ophthalmol.; 101: 1122-1126.*
Greiner et al., "A comparison of the clinical efficacy of pheniramine maleate/naphazoline hydrochloride ophthalmic solution and olopatadine hydrochloride ophthalmic solution in the conjunctival allergen challenge model", *Clin. Ther.* 27(5):568-577 (2005).
Ono et al., "Allergic conjunctivitis: Update on pathophysiology and prospects for future treatment", *J. All. Clin. Imm.* 115(1):118-122 (2005).
Database WPI Week 200335, Thomson Scientific, London, GB; AN 2003-367023 (XP002527205); & JP 2002 308775 (abstract).
Database WPI Week 200169, Thomson Scientific, London, GB; AN 2001-605287; & JP 2001 187728 (abstract).
Database WPI Week 200663, Thomson Scientific, London, GB; AN 2006-607199; & JP 2006 232792 (abstract).
American Society for Aesthetic Plastic Surgery (ASAPS), News Release "2002 ASAPS Statistics: Nearly 6.9 Million Cosmetic Procedures", Mar. 4, 2003, 2 pages.
Beltrani, V.S., "Eyelid Dermatitis", *Curr. Allergy Asthma Rep.*, 1:380-388 (2001).
Berge et al., "Pharmaceutical Salts", *J. Pharm. Sci.*, 66(1):1-19 (1977).
Bielory, L., "Allergic and immunologic disorders of the eye. Part II: Ocular allergy", *J. Allergy Clin. Immunol.*, 106(6):1019-1032 (2000).
Carter, B.B., "Eye Swelling and Pain: A Chinese Herbal Case Study", http://www.pulsemed.org/eyepainswelling.htm, pp. 1-3 (1999).
Chen et al., "Periorbital edema as an initial presentation of rosacea", *J. Am. Acad. Dermatol.*, 37(2):346-348 (1997).
Dupouy-Camet et al., "Opinion on the diagnosis and treatment of human trichinellosis", *Expert Opin. Pharmacother.*, 3(8):1117-1130 (2002).

(Continued)

*Primary Examiner* — Carlos Azpuru
*Assistant Examiner* — David Browe
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The invention features novel topical ophthalmic formulations comprising an osmotically active agent and a vasoconstrictor. Suitable osmotically active agents for use in the ophthalmic formulations of the invention include, without limitation, sodium chloride, dextrose, glycerine, sucrose, mannitol, and sorbitol; suitable vasoconstritors include, without limitation, naphazoline and oxymetazoline. Also provided are methods of using the ophthalmic formulations of the invention for the treatment and prevention of eyelid swelling by administering the ophthalmic formulations of the invention to the eye surface of a subject in need thereof.

3 Claims, 17 Drawing Sheets

(56) References Cited

OTHER PUBLICATIONS

Greiner et al., "Effects of Eye Rubbing on the Conjunctiva as a Model of Ocular Inflammation", *Am. J. Ophthalmol.*, 100:45-50 (1985).

Jacobson, D.M., "Dysthyroid Orbitopathy", *Seminars in Neurology*, 20(1):43-54 (2000).

Juniper et al., "Clinical aspects of allergic disease—Assessment of quality of life in adolescents with allergic rhinoconjunctivitis: Development and testing of a questionnaire for clinical trials", *J. Allergy Clin. Immunol.*, 93(2):413-423 (1994).

Kolker, A.E., "Hyperosmotic agents in glaucoma", *Investigative Ophthalmology*, 9(6):418-423 (1970).

Langley et al., "Unilateral Blepharochalasis", *Ophthalmic Surgery*, 18(8):594-598 (1987).

Smith et al., "Malignant Lymphoma Presenting as Bilateral Swelling of the Eyelid", *J. Med. Soc.* New Jersey, 74(11):968-970 (1977).

Wobig, J., "Eyelid Anatomy", in Cosmetic Oculoplastic Surgery, Chapter 7, pp. 78-87 (1982).

Zide et al., "The eyelids", in Surgical Anatomy of the Orbit, Chapter 3, pp. 21-32, Raven Press, New York (1985).

Jiten, Taishiyuuyaku. "Ippan you iyakuhinshiyuu (nonprescripton drugs)." *Encyclopedia of Self-Medication 2006-'07.* (Apr. 10, 2006) : 238-239.

Jiten, Taishiyuuyaku. "Ippan you iyakuhinshiyuu (nonprescription drugs)." *Encyclopedia of Self-Medication 2004-'05.* (Apr. 9, 2004) : 251-252, 258-259.

Kabushiki et al. Ophthalmic Astringent, Ophthaline P, Zinc Sulfate Ophthalmic Solution (1999).

\* cited by examiner

CONDITIONS THAT PRESENT EYELID SWELLING

| CONDITION | EYELID PRESENTATION | OTHER EARLY OCULAR CHARACTERISTICS OF PRESENTING SIGN |
|---|---|---|
| Wegener's | Granulomatosis Unilateral swelling of upper lid | Exophthalmos, diplopia |
| Kimura's Disease | Bilateral lid swelling | Mass lesions, elevated IgE, eosinophil and lymphocyte infiltration |
| Conjunctival amyloidosis | Diffuse bilateral lid swelling | Amyloid deposits (group of disorders) |
| Orbital sarcoid | Lid swelling | Diplopia, conjunctival, retinal, optic nerve, and lacrimal gland involvement |
| Kikuchi's disease (necrotizing histiocytic lymphadenitis) | Lid swelling | Additional cutaneous manifestations (nonspecific) |
| Pediatric leukemia | Unilateral swelling of lower lid A | Acute dacryocystitis, preseptal cellulitis |
| Rosai-Dorfman disease | Lid swelling | Ocular presentation rare (11%), orbital |
| Rosacea | Periorbital edema | Blepharitis, conjunctivitis |
| Hemophagocytic syndrome | Unilateral swelling of upper lid | Bilateral visual disturbance, optic disk edema, retinal hemorrhages, perivenous retinal white patches |
| Melkersson-Rosenthal syndrome | Lid swelling | Facial edema, facial paralysis, furrowed tongue, perilymphatic granulomas, dermal edema |
| Acute infectious mononucleosis | Periorbital edema and lid swelling | Occur approximately one week prior to other |
| Blepharochalasis syndrome | Recurrent, intermittent eyelid swelling, typically bilateral | Leaves lids with stretched excess skin, aged appearance |
| Nephrotic syndrome | Bilateral lid swelling | Swollen face |
| Chronic dacryoadenitis | Intermittent swelling of upper lid | Nonspecific |
| Seborrheic dermatitis | Lid swelling | Blepharitis, scalp involvement, red lid margins |
| Lymphoma | Lid swelling/mass | Enlarged lymph nodes |

Fig. 1

METHOD FOR THE TREATMENT AND PREVENTION OF EYELID SWELLING

RELATED APPLICATIONS

This application claims the benefit of U.S. Provisional Application No. 60/794,983, filed Apr. 26, 2006 and U.S. Provisional Application No. 60/845,479, filed Sep. 18, 2006, the contents of which are hereby incorporated by reference in their entirety.

FIELD OF THE INVENTION

The present invention relates to novel ophthalmic compositions and methods useful for the prevention and treatment of eyelid swelling. Specifically, the invention relates to an ophthalmic composition comprising an osmotically active agent, an astringent, a vasoconstrictor, or a combination thereof, useful for the prevention and treatment of eyelid swelling. The invention additionally relates to methods of administering such compositions to a subject in need thereof.

BACKGROUND OF THE INVENTION

Eyelid swelling and inflammation of the lids has both long and short-term significance in terms of histologic impact, patient quality of life, and general patient comfort. The human eyelid is made of the thinnest skin layers of the body, the most well-defined layers of tissues and muscles, and the most fragile collagen fibers. Because of these delicate skin layers, the eyelid is very susceptible to swelling, acute inflammation, and possible long-term damage.

The eyelids have several important roles that allow the eye to function as it does. They protect the eye and shield the cornea by reflexive closing. It is this mechanism that often prevents the entry of particles or foreign objects into the eye and possible damage. The lids also control the amount of light that enters the eye, just as a shutter in a camera does. They also add to the components of the tear film (via the lid margin) and maintain distribution of the smooth liquid over the eye by their spreading action during blinking. The eyelids play a very large role in maintaining not only the health of the eye, but the overall function of the ocular system. When inflammation of this crucial protection mechanism occurs, the ocular health of the individual is compromised.

Repeated stretching and damage to the lids as a result of swelling of various etiologies can cause the temporary development of sagging, drooping skin layers above and below the eye. This swelling of the lids can provide a very undesirable appearance and can even restrict the field of vision. While these signs are often only temporary, the actual damage that occurs on the physiologic and anatomic levels can eventually result in permanent changes because it accumulates with each recurrence.

This symptom of eyelid swelling is not often considered to be of primary concern when assessing ocular health, although it is a major concern for many patients, physicians and researchers. Morning eyelid swelling is very common and has both extensive social concerns in addition to concerns relating to patient health. Patients' annoyance and overall intolerance with puffy, sagging eyelids is clearly shown by the fact that eyelid surgery (229,092) and botulinum toxin injection (1,658,667) were two of the most common procedures performed by plastic surgeons in the U.S. in 2002. Despite this significant desire to reduce the presence of eyelid edema, there has been a lack of attention to the symptom. It is often classified among other signs and symptoms but is rarely a primary variable in clinical studies, as historically it has been difficult to precisely measure. Various ocular allergy medications, like olopatadine 0.1% (Patanol) begin to reduce eyelid swelling relating to allergic conjunctivitis, but there is no medication available to specifically combat this symptom directly and effectively. With such a powerful presence of so many forms in society, a treatment that directly impacts the condition of lid swelling is necessary.

SUMMARY OF THE INVENTION

Provided are novel compositions and methods for treating and preventing eyelid swelling. In certain embodiments, novel topical ophthalmic formulations comprising an osmotically active agent and/or a vasoconstrictor and/or an astringent agent is provided. In a particular the invention provides topical ophthalmic formulations comprising a combination of an osmotically active agent and/or a vasoconstrictor and/or astringent agent, which act synergistically to treat and prevent eyelid swelling. Optionally, the osmotically active agent, and/or vasoconstrictor, and/or astringent agent is combined with various other agents, for use in treating and preventing eyelid swelling.

In some embodiments, the compositions of the invention comprise an osmotically active agent including but not limited to a colloidal osmotic agent and a crystalloid osmotic agent. Crystalloid osmotic agents suitable for use in the compositions of the invention include but are not limited to sodium chloride (NaCl), dextrose, sucrose, glycerin, mannitol, sorbitol, polyethylene glycol 3350 NF, magnesium citrate and lactulose. In certain embodiments, the effective amount of the crystalloid osmotic is selected from the group consisting of: about 1% to about 10% sodium chloride, about 1% to about 10% dextrose, about 1% to about 20% glycerine, about 1% to about 20% mannitol, about 1% to about 95% sucrose, and about 1% to about 95% sorbitol. Preferably, the crystalloid osmotic is sodium chloride, and the effective amount is about 1% to about 10%, more preferably about 2% to about 5%.

Colloidal osmotic agents suitable for use in the compositions of the invention include but are not limited to: hetastarch, pentastarch, gelatin polypeptides cross-linked with urea, dextran 70, dextran 40, albumin, icodextrin, bentonite USP, MgAl silicate NF type 2A, alginic acid/sodium alginate NF, microcrystalline cellulose and CMC NF, carbomer and gellan gum.

In certain embodiments, the effective amount of the colloidal osmotic is selected from the group consisting of: about 1% to about 10% hetastarch, about 1% to about 20% pentastarch, about 1% to about 10% dextran 70, about 1% to about 10% dextran 40, about 1% to about 50% albumin, and about 1% to about 50% microcrystalline cellulose.

In some embodiments, the compositions of the invention comprise a vasoconstrictor. Vasoconstrictors suitable for use in the compositions of the invention include but are not limited to naphazoline, oxymetazoline, phenylephrine and tetrahydrozoline. In a preferred embodiment, the vasoconstrictor is naphazoline and the effective amount is about 0.01% to about 0.5%, more preferably about 0.01% to about 0.2%.

In still other embodiments, the compositions of the invention comprise an astringent agent. Astringents suitable for use in the compositions of the invention include but are not limited to witch hazel, zinc sulfate, silver sulfate, plant tannins, oak bark extract, pentagalloyl glucose, alum, burow's solution, black thorn extract, bird cherry extract and natural flavanoids. Preferably, the astringent agent is witch hazel and/or zinc sulfate 0.25%.

In a certain embodiment, the compositions of the invention comprise a combination of an osmotically active agent and a vasoconstrictor. In a preferred embodiment, the osmotically active agent is sodium chloride, and the vasoconstrictor is naphazoline. Preferably, the sodium chloride is present in the range of about 1% to about 10%, more preferably about 2% to about 5%, and the naphazoline is present in the range of about 0.01% to about 0.5%, more preferably about 0.01% to about 0.2%.

The compositions of the invention may be formulated for topical administration as solutions, suspensions, oils, viscous or semi-viscous gels, emulsions, liposomes, lotions, ointments, creams, gels, salves, powders, sustained or slow release formulations, eyelid lotions, or other types of solid or semi-solid compositions, and in sprayable form. The compositions of the invention may be formulated for acute or chronic dosing for the treatment and/or prevention of eyelid swelling.

The invention also features novel methods of treating and preventing eyelid swelling with these formulations. In some embodiments the method of treating and preventing eyelid swelling in a subject comprises topically administering a composition of the invention to the eye surface of a subject to treat and prevent eyelid swelling. In other embodiments, the method of the invention comprises topically administering a composition of the invention to the inner and/or outer eyelid of a subject to treat and prevent eyelid swelling.

In some embodiments, the method of treating and preventing eyelid swelling in a subject comprises: administering to the eye surface of the subject an effective amount of at least one active agent selected from the group consisting of: an osmotically active agent, a vasoconstrictor, and an astringent agent.

In some embodiments, the method of treating and preventing eyelid swelling in a subject comprises administering an osmotically active agent including but not limited to a colloidal osmotic agent and/or a crystalloid osmotic agent to the eye surface of a subject. Crystalloid osmotic agents suitable for use in the methods of the invention include but are not limited to sodium chloride (NaCl), dextrose, sucrose, glycerin, mannitol, sorbitol, polyethylene glycol 3350 NF, magnesium citrate and lactulose. In certain embodiments, the effective amount of the crystalloid osmotic is selected from the group consisting of: about 1% to about 10% sodium chloride, about 1% to about 10% dextrose, about 1% to about 20% glycerine, about 1% to about 20% mannitol, about 1% to about 95% sucrose, and about 1% to about 95% sorbitol. Preferably, the crystalloid osmotic is sodium chloride, and the effective amount is about 1% to about 10%, more preferably about 2% to about 5%.

Colloidal osmotic agents suitable for use in the methods of the invention include but are not limited to: hetastarch, pentastarch, gelatin polypeptides cross-linked with urea, dextran 70, dextran 40, albumin, icodextrin, bentonite USP, MgAl silicate NF type 2A, alginic acid/sodium alginate NF, microcrystalline cellulose and CMC NF, carbomer and gellan gum.

In certain embodiments, the effective amount of the colloidal osmotic is selected from the group consisting of: about 1% to about 10% hetastarch, about 1% to about 20% pentastarch, about 1% to about 10% dextran 70, about 1% to about 10% dextran 40, about 1% to about 50% albumin, and about 1% to about 50% microcrystalline cellulose.

In some embodiments, the method of treating and preventing eyelid swelling in a subject comprises administering a vasoconstrictor to the eye surface of the subject. Vasoconstrictors suitable for use in the methods of the invention include but are not limited to naphazoline, oxymetazoline, phenylephrine, and tetrahydrozoline. In a preferred embodiment, the vasoconstrictor is naphazoline and the effective amount is about 0.01% to about 0.5%, more preferably about 0.01% to about 0.2%.

In still other embodiments, the method of treating and preventing eyelid swelling in a subject comprises administering an astringent agent to the eye surface of a subject. Astringents suitable for use in the compositions of the invention include but are not limited to witch hazel, zinc sulfate, silver sulfate, plant tannins, oak bark extract, pentagalloyl glucose, alum, burow's solution, black thorn extract, bird cherry extract and natural flavanoids. Preferably, the astringent agent is witch hazel and/or zinc sulfate 0.25%.

In a certain embodiment, the method of treating and preventing eyelid swelling in a subject comprises administering a combination of an osmotically active agent and a vasoconstrictor to the eye surface of a subject. In a preferred embodiment, the osmotically active agent is sodium chloride, and the vasoconstrictor is naphazoline. Preferably, the sodium chloride is present in the range of about 1% to about 10%, more preferably about 2% to about 5%, and the naphazoline is present in the range of about 0.01% to about 0.5%, more preferably about 0.01% to about 0.2%.

Such formulations may be administered at an appropriate dosage depending on absorption, inactivation, and excretion rates of the drug and the delivery rate of the compound during the daytime, night-time, immediately before bedtime, and/or immediately upon awakening, to treat and prevent eyelid swelling. Such formulations may also be administered for acute or chronic use to treat and prevent eyelid swelling.

Further, the invention features a method for measuring changes in eyelid swelling using a controlled objective technique that utilizes scanning imaging technology (e.g., 3D scanning technology). Such methods enable an objective and precise quantification of daily fluctuation in lid swelling.

Even further, the invention features kits for the shipping, storage or use of the formulations, as well the practice of the methods. Other features and advantages of the invention will become apparent from the following detailed description and claims.

BRIEF DESCRIPTION OF THE DRAWINGS

FIG. 1 contains a partial table of medical conditions that present eyelid swelling, details of such presentation for each condition and other symptoms of such conditions.

Figure 5:
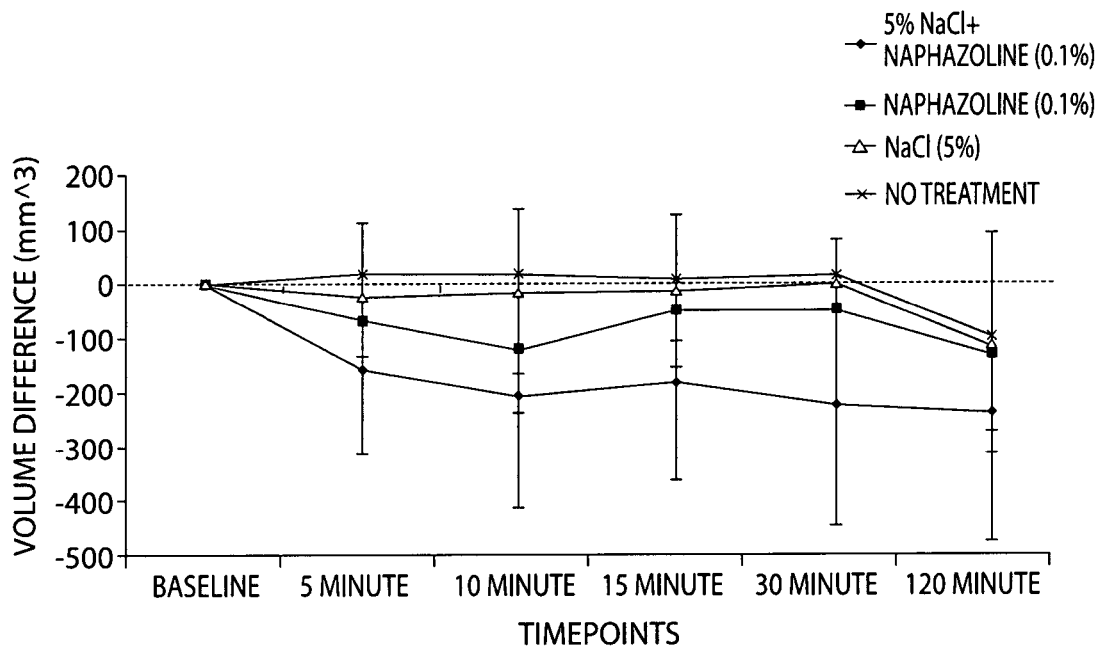
FIG. 5 is a line graph depicting the results of a study comparing the efficacy of a combination of naphazoline 0.1% and 5% NaCl solution with naphazoline 0.1% or NaCl 5% individually, (and no treatment control) for treatment of morning lid swelling.
Figure 6:
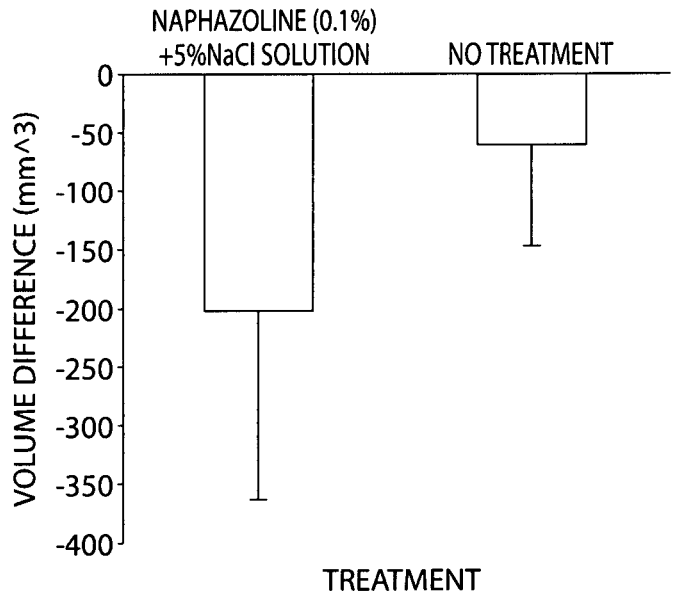

FIG. 6 is a bar graph depicting the combination of naphazoline 0.1% and 5% NaCl results of the study shown in FIG. 5.

Figure 7:
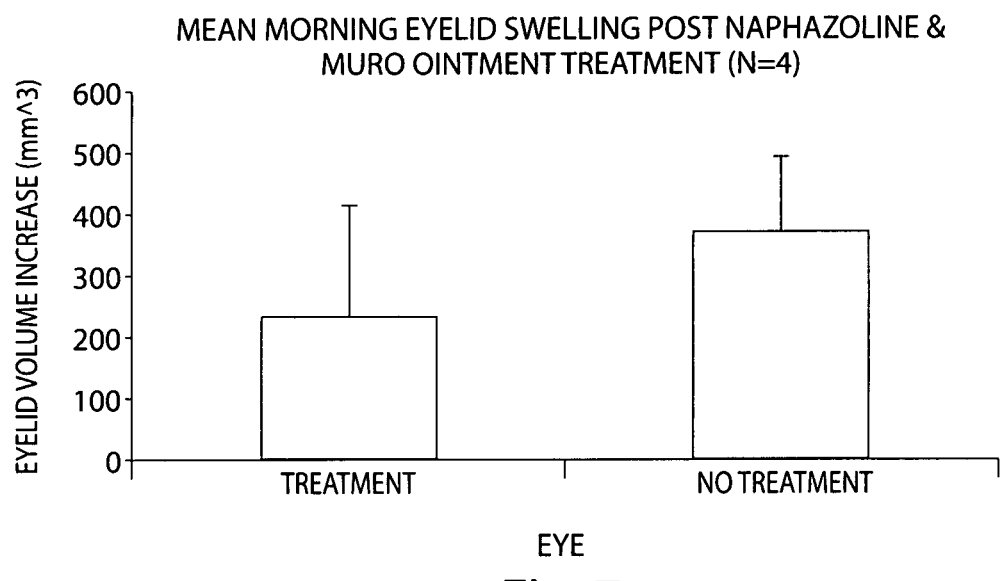

FIG. 7 is a bar graph depicting the results of a study evaluating the efficacy of a combination of naphazoline hydrochloride (0.05%) dissolved in 5% NaCl ophthalmic ointment for treatment of morning eyelid swelling in 4 subjects.

Figure 8:
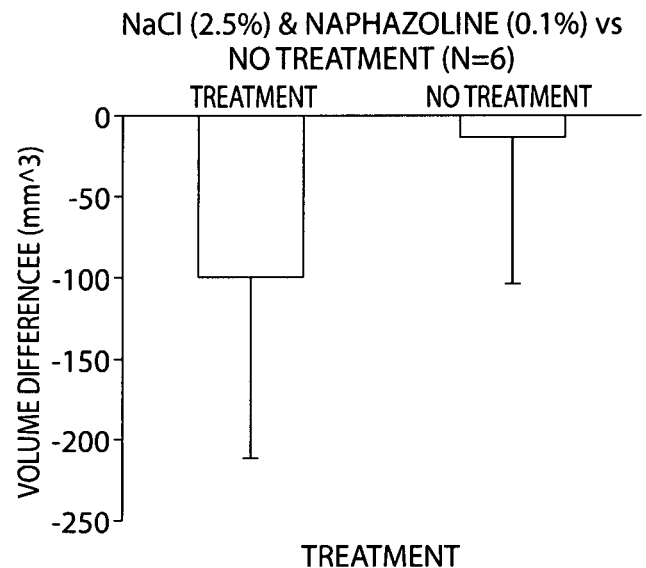

FIG. 8 is a bar graph depicting the results of a study evaluating the efficacy of a combination of naphazoline hydrochloride (0.1%) dissolved in 2.5% NaCl ophthalmic solution for treatment of morning eyelid swelling in 6 subjects. Error bars represent one standard error.

Figure 9:
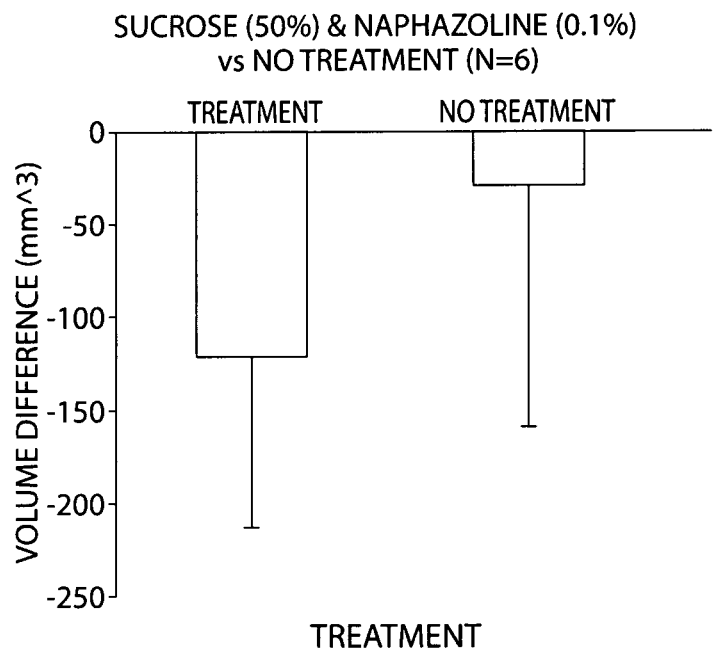

FIG. 9 is a bar graph depicting the results of a study evaluating the efficacy of a combination of naphazoline hydrochloride (0.1%) in 50% sucrose solution for treatment of morning eyelid swelling in 6 subjects. Error bars represent one standard error.

Figure 10:
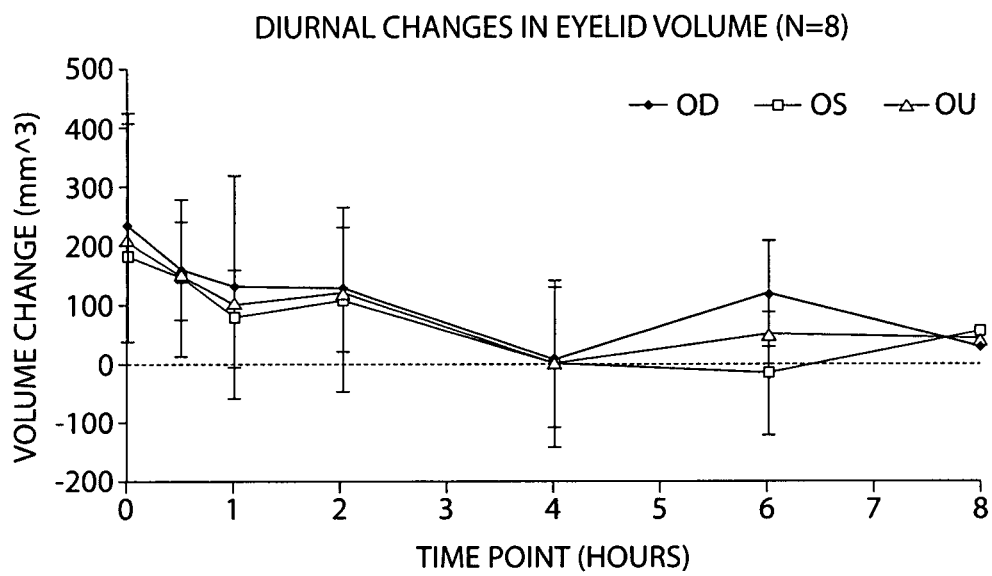

FIG. 10 is a line graph depicting the natural progression of morning eyelid swelling. No treatment was administered in this experiment.

Figure 11:
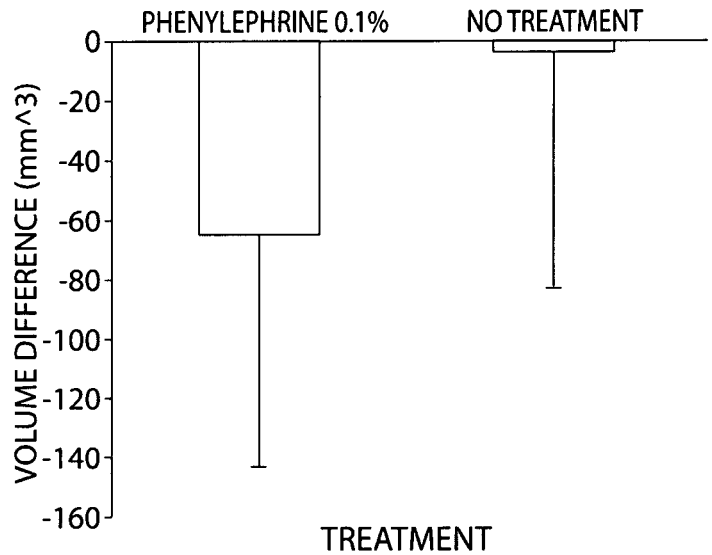

FIG. 11 is a bar graph depicting the results of a study evaluating the efficacy of a phenylephrine 0.1% ointment for treatment of morning eyelid swelling in 6 subjects. Error bars represent one standard error.

Figure 12:
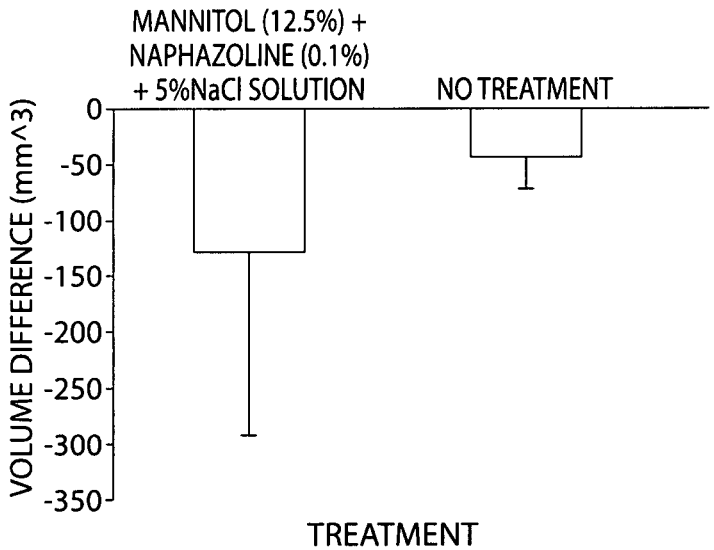

FIG. 12 is a bar graph depicting the results of a study evaluating the efficacy of a combination of naphazoline hydrochloride (0.1%) dissolved in 5% NaCl and 12.5% mannitol ophthalmic solution for treatment of morning eyelid swelling in 6 subjects. Error bars represent one standard error.

Figure 13:
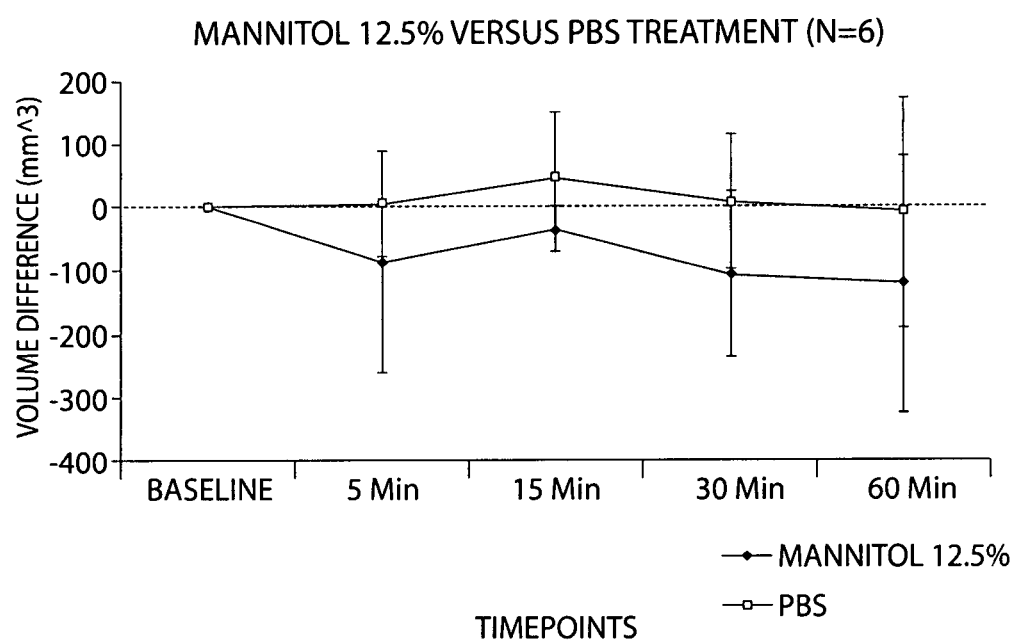

FIG. 13 is a line graph depicting the results of a study evaluating the efficacy of 12.5% mannitol ophthalmic solution for treatment of morning eyelid swelling in 6 subjects. Error bars represent one standard error.

DETAILED DESCRIPTION OF THE INVENTION

1. Definitions

For convenience, before further description of the present invention, certain terms employed in the specification, examples, and appended claims are collected here. These definitions should be read in light of the remainder of the disclosure and understood as by a person of skill in the art.

As used herein, the term "antiallergenic agent" refers to a molecule or composition that treats ocular allergy or reduces a symptom of ocular allergy. Examples of antiallergenic agents include, but are not limited to, "antihistamines" or drugs which block histamine from binding to the histamine receptors, "mast cell stabilizers" or drugs that block the release of histamine and other substances from the mast cell, "drugs with multiple modes of action" or drugs that are antiallergenic agents having multiple modes of action (e.g. drugs that are antihistamines and mast cell stabilizers, drugs with antihistamine, mast cell stabilizing and anti-inflammatory activity, etc.), and nonsteroidal anti-inflammatory drugs or "NSAIDs" and steroids.

The term "aqueous" typically denotes an aqueous composition wherein the carrier is to an extent of >50%, more preferably >75% and in particular >90% by weight water.

The phrase "effective amount" is an art-recognized term, and refers to an amount of an agent that, when incorporated into a pharmaceutical composition of the present invention, produces some desired effect at a reasonable benefit/risk ratio applicable to any medical treatment. In certain embodiments, the term refers to that amount necessary or sufficient to eliminate, reduce or maintain (e.g., prevent the spread of) eyelid swelling, or prevent or treat eyelid swelling. The effective amount may vary depending on such factors as the disease or condition being treated, the particular composition being administered, or the severity of the disease or condition. One of skill in the art may empirically determine the effective amount of a particular agent without necessitating undue experimentation. For the treatment of eyelid swelling, an effective amount preferably refers to the amount of a therapeutic agent that reduces eyelid swelling by at least 2%, at least 5%, at least 10%, at least 15%, at least 20%, at least 30%, at least 35%, at least 40%, at least 45%, at least 50%, at least 60%, at least 65%, at least 70%, at least 75%, at least 80%, at least 85% at least 90%, at least 95%, or at least 100%, as determined by a ruler, subjective scales assessing eyelid swelling (for example, but not limited to, subjective clinical scales that determine swelling as mild, moderate, severe, or 0, 1, 2, or 3, or other appropriate scale), and/or 3D scanning technology.

The term "eyelid swelling" refers to any condition comprising the swelling or inflammation of the eyelids, including periorbital edema. For example, all of the conditions listed in FIG. 1 are encompassed within the term "eyelid swelling." Thus, "eyelid swelling" as defined herein encompasses any cause of eyelid swelling ranging from uncommon disorders like blepharochalasis, to the more common dermatochalasis, characterized by "bags under the eyes." In addition to these swelling infections, there are many other conditions that can result in swelling of the eyelids, including, but not limited to, rosacea, dermatitis caused by cosmetics or topical pharmaceuticals, lymphoma, renal and endocrine dyfunctions (thyroid), and even trichinosis, an infectious disease for which the chronic periocular edema can be a very useful diagnostic sign. More common causes of eyelid swelling include allergies, age, alcohol use, computer use, reading, fatigue and diurnal variations (morning eyelid swelling.) Further, ocular allergies are one of the most common causes of eyelid inflammation, with almost 20% of the general population being affected. In this case, the array of pre-formed mediators released as a result of IgE-stimulated mast cell degranulation are responsible for the clinical signs and symptoms of an allergic reaction causing vasodilation of the vasculature and leakage of fluid from the blood stream to the tissue. Morning eyelid swelling occurs overnight and results in eyelid swelling in the morning upon awakening.

The term "hyperosmotic solution" as used herein refers to any solution having an osmolality greater than another fluid, e.g., that comprises a higher concentration of osmotically active components than the other fluid.

The term "ocular allergy" as used herein refers to any allergic disease of the eye. Examples of such ocular allergies include but are not limited to seasonal/perennial allergic conjunctivitis, vernal keratoconjunctivitis, giant papillary conjunctivitis, perennial allergic conjunctivitis and atopic keratoconjunctivitis. The signs and symptoms of ocular allergies include chemosis, eye itching, redness, tearing, and eyelid swelling.

The term "osmotically active agent" refers to a water-attracting agent, e.g., a hygroscopic, hydroscopic or other agent, which drives the osmotic flow in a hyperosmotic solution.

A "patient," "subject," or "host" to be treated by the subject method refers to either a human or non-human animal, such as primates, mammals, and vertebrates.

The phrase "pharmaceutically acceptable" is art-recognized and refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) aqueous solutions, suspensions, ointments, and (22) other non-toxic compatible substances employed in pharmaceutical formulations.

The term "pharmaceutically acceptable salts" is art-recognized, and refers to relatively non-toxic, inorganic and organic acid addition salts of compositions of the present invention or any components thereof, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include but are not limited too the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1-19 (1977).

The term "preventing," when used in relation to a condition, is art-recognized, and refers to administration of a composition which reduces the frequency of, or delays the onset of, symptoms of a medical condition in a subject relative to a subject which does not receive the composition.

The term "treating" is an art-recognized term which refers to curing and/or ameliorating at least one symptom of any condition or disease by administering one or more diagnostic, therapeutic, or prophylactic agents, including but not limited to ocular agents such as osmotically active agents, vasoconstrictors, astringent agents, and a combination thereof.

The term "vasoconstrictors" refers to any drug or agent that constricts blood vessels, including but not limited to agents that act on alpha-1 receptors in smooth muscle tissues.

2. Eyelid Swelling

Eyelid swelling can occur as a result of a number of different pathological conditions including allergy, infection, mild irritation/inflammation and trauma, however morning eyelid swelling may be most common. Morning eyelid swelling occurs as a result of lost tissue turgor and inflammation. As an individual ages, the skin surrounding the eyelids loses its elasticity. The collagen fibers that provide the dermis with rigidity and elasticity begin to break down, a natural process that can be exacerbated by excessive exposure to sunlight or other destructive environmental stimuli such as smoke. In addition, underlying orbital fat is broken down, leading again to the development of flaccid, empty appearing tissue, or lost tissue turgor.

When an individual sleeps in a horizontal position, fluid leaks out of the underlying vasculature into the empty, structureless tissue surrounding the eyes, in particular the lower eyelid. This may be caused by accumulation of inflammatory mediators in the tear film and conjunctiva. The lost elasticity of the dermis allows the superficial eyelid tissue to expand with the increase in fluid. When the individual awakens, the eyelids appear puffy and swollen as a result of the excess fluid that has drained into the broken down eyelid tissue. Variable fluid accumulation may occur in the tissues overlying the orbital bone at the outer corner of the lower eyelid. This fluid may appear dark blue, or purple in color, contributing the appearance or tired, baggy eyes. After an individual awakens and assumes an upright position, eyelid swelling gradually decreases as fluid drains out of the eyelid tissue. However, this process can take a considerable amount of time.

Eyelid swelling and periorbital edema is distinguishable from other types of ocular edema, such as corneal edema. As described, eyelid swelling develops as a result of fluid leaking from the underlying vasculature within the orbital and periorbital region. In contrast, the cornea does not contain blood vessels. Corneal edema typically results from abnormal intraocular pressure, electrolyte imbalance within the corneal stroma, and/or the presence of an active metabolic pump in the endothelium, each of which drives fluid into the cornea. As such, a pharmaceutical composition comprising an effective amount of an active agent selected from an osmotically active agent, a vasoconstrictor, an astringent agent, or combinations thereof, which is instilled directly into the eye is effective to treat eyelid swelling by "drying out" the underlying vasculature to treat and prevent leakage into the eyelid tissue and periorbital region. A pharmaceutical composition comprising an effective amount of an active agent selected from an osmotically active agent, a vasoconstrictor, an astringent agent, or combinations thereof, which is applied to the inner and/or outer surface of the eyelid is also effective to treat and prevent eyelid swelling.

3. Pharmaceutical Compositions

Figure 2:
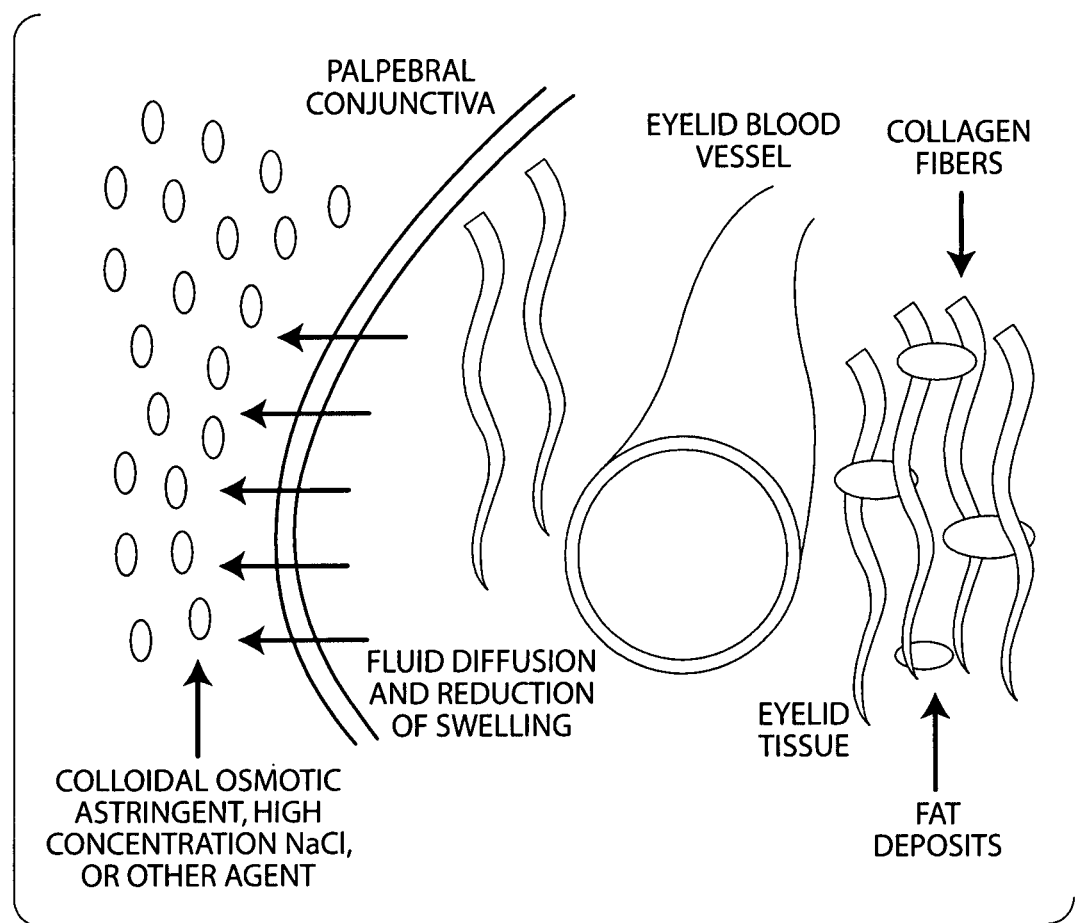
FIG. 2 depicts the effect of an osmotic agent on eyelid swelling.

Featured are novel topical pharmaceutical compositions comprising an effective amount of one or more active agents in a pharmaceutically acceptable carrier for the treatment and prevention of eyelid swelling and periorbital edema. Such formulations provide a comfortable formulation when instilled in the eye. The one or more active agents may include, but are not limited to, osmotically active agents, vasoconstrictors, astringent agents, or combinations thereof. The astringent or osmotically active agent may pull fluid out of swollen or inflamed tissue (FIG. 2), while a vasoconstrictor may prevent additional leakage from the underlying vasculature into the eyelid tissue.

In one embodiment, the active agent is an osmotically active agent. In certain embodiments, the pharmaceutical composition comprises a hyperosmotic solution containing an osmotically active agent. Hyperosmotic solutions contain a higher concentration of electrolytes than that found in body cells.

In certain embodiments, the osmotically active agent is a crystalloid osmotic agent. Examples of crystalloid osmotics include, but are not limited to, sodium chloride (NaCl), dextrose, glycerin, mannitol, sorbitol, sucrose, polyethylene glycol 3350 NF, magnesium citrate and lactulose.

In certain embodiments, the crystalloid osmotic agent is mannitol. Mannitol is a sugar alcohol form of mannose that occurs naturally in many fruits and vegetables.

In other embodiments, the crystalloid osmotic agent is glycerin. Glycerin is obtained from fats and oils as a byproduct of saponification and is frequently used as a solvent for many ophthalmic products and as a component of a variety of products including cosmetics, soaps, and lubricants.

In a particular embodiment, the crystalloid osmotic agent is sodium chloride (solution, gel, suspension, or other pharmaceutically acceptable vehicle).

In still other embodiments, the crystalloid osmotic agent is dextrose. Dextrose is approved for injection in adults and pediatric patients as a source of electrolytes, calories and water for hydration.

In still other embodiments, the crystalloid osmotic agent is polyethylene glycol 3350 NF.

In still other embodiments, the crystalloid osmotic agent is magnesium citrate.

In still other embodiments, the crystalloid osmotic agent is lactulose. Lactulose is a synthetic sugar.

In certain embodiments, the osmotically active agent is a colloidal osmotic. Examples of colloidal osmotics include, but are not limited to, hetastarch, pentastarch, gelatin polypeptides cross-linked with urea, dextran 70, dextran 40, albumin, icodextrin, bentonite USP, MgAl silicate NF type 2A, alginic acid/sodium alginate NF, microcrystalline cellulose and CMC NF, carbomer and gellan gum.

In certain embodiments, the colloidal osmotic agent is hetastarch. Hetastarch is a plasma expander indicated for treatment of shock due to fluid loss.

In still other embodiments, the colloidal osmotic agent is pentastarch. Like hetastarch, pentastarch is a plasma expander indicated for treatment of shock due to fluid loss.

In still other embodiments, the colloidal osmotic agent is a combination product of gelatin polypeptides cross linked with urea.

In still other embodiments, the colloidal osmotic agent is Dextran 70.

In other embodiments, the colloidal osmotic agent is Dextran 40. Like Dextran 70, Dextran 40 is indicated for fluid replacement in shock.

In still other embodiments, the colloidal osmotic agent is albumin.

In still other embodiments, the colloidal osmotic agent is Icodextrin. Icodextran is a sucrose derivative that is frequently used for osmotic applications as a substitute for glucose.

In still other embodiments the colloidal osmotic agent is MgAl Silicate NF Type 2A.

In still other embodiments the colloidal osmotic agent is alginic acid. Alginic acid is a viscous gum that is isolated from seaweed and can be used as an osmotic agent.

In still other embodiments, the colloidal osmotic agent is carboxymethylcellulose sodium (CMC) NF.

In still other embodiments, the colloidal osmotic agent is gellan gum.

In still other embodiments, the colloidal osmotic is sodium carbomer.

In still other embodiments, the colloidal osmotic agent is microcrystalline cellulose.

There are fundamental differences between colloids and crystalloids in their formulation. Crystalloids are predominately based on a solution of sterile water with added electrolytes. Crystalloids come in a variety of formulations, from those that are hypotonic to plasma to those that are isotonic or hypertonic. Colloids are often based on crystalloid solutions, thus containing water and electrolytes, but have the added component of a colloidal substance (e.g., a suspension of particles smaller than one millimicron in diameter that does not freely diffuse across a semipermeable membrane).

Other exemplary osmotically active agents which may comprise the compositions of the invention include compounds such as Visine AC® (which contains tetrahydrozaline (vasoconstrictor) and zinc sulfate (astringent)), magnesium sulfate, magnesium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid- and soluble carbohydrates such as raffinose, glucose, mixtures thereof and the like.

In certain embodiments, the active agent is an astringent agent (that is, an agent that among other things, shrinks tissue). Examples of astringent agents include, but are not limited to, witch hazel, zinc sulfate, silver sulfate, plant tannins, oak bark extract, pentagalloyl glucose, alum, burow's solution, black thorn extract, bird cherry extract and natural flavanoids.

In a particular embodiment, the astringent is witch hazel. Witch hazel is an isolate from an herb found in central and southern Europe.

In another particular embodiment, the astringent agent is zinc sulfate.

In still another particular embodiment, the astringent is silver sulfate.

In certain embodiments, the active agent is a vasoconstrictor. In one embodiment, the vasoconstrictor is an alpha-1 adrenergic agonist. In other embodiments, the vasoconstrictor is any agent that decreases the diameter of the blood vessel and thus prevents leakage. Alpha-1 adrenergic agonists contemplated for use in the topical pharmaceutical compositions of the invention include but are not limited to naphazoline, oxymetazoline, phenylephrine, and tetrahydrozoline. In a particular embodiment, the vasoconstrictor is naphazoline. In another particular embodiment, the vasoconstrictor is oxymetazoline. Like naphazoline, oxymetazoline binds to alpha-1 receptors to induce smooth muscle contraction.

In another certain embodiment, the pharmaceutical composition of the invention comprises both a vasoconstrictor and an osmotically active agent. In a particular embodiment, the pharmaceutical composition of the invention comprises both naphazoline and NaCl. The extraordinary efficacy of such formulations is attributed to, among other things, the synergistic effect of the combination of ingredients in them, as described in the Examples below.

The effective amount of an active agent may be present in the composition at a dose in the range of about 0.001% to about 100.0%. For example, the effective amount of each active agent may be in the range of about 0.001% to about 0.01%, of about 0.01% to about 0.100%, of about 0.100% to about 1.0%, of about 1.00% to about 10.00%, or of about 10% to about 100%.

One of ordinary skill in the art will recognize that the effective amount of an active agent present in the formulations of the invention will vary depending on the nature of the active agent(s) used, depending on factors including but not limited to absorption, inactivation, and excretion rates of the drug, the delivery rate of the compound, and the one or more combinations of agents. For example, an effective amount of sodium chloride is in the range of about 1% to about 10%, preferably about 1% to about 6%, more preferably about 2% to about 5%. An effective amount of dextrose is in the range of about 1% to about 10%, preferably about 1% to about 6%, more preferably about 2% to about 5%. An effective amount of sucrose is about 1% to about 95%, preferably about 10% to about 90%, more preferably about 20% to about 80%, even more preferably about 30% to about 70%. An effective amount of glycerine is in the range of about 1% to about 30%, preferably 1% to about 20%, more preferably about 1% to about 10%. An effective amount of mannitol is in the range of about 1% to about 30%, preferably about 1% to about 20%, more preferably about 10% to about 15%. An effective amount of sorbitol is in the range of about 1% to about 100%, preferably about 10% to about 90%, more preferably about 20% to about 80, even more preferably about 30% to about 70%. An effective amount of hetastarch is in the range of about 1% to about 20%, preferably about 1% to about 10%, more preferably about 4% to about 6%. An effective amount of pentastarch is in the range of about 1% to about 20%, preferably about 5% to about 15%, more preferably about 5% to about 10%. An effective amount of dextran 70 is in the range of about 1% to about 20%, preferably about 1% to about 10%, more preferably about 4% to about 6%. An effective amount of dextran 40 is in the range of about 1% to about 20%, preferably about 1% to about 10%, more preferably about 4% to about 6%. An effective amount of albumin is in the range of about 10% to about 50%, preferably about 15% to about 30%, more preferably about 20% to 30% albumin. An effective amount of naphazoline is in the range of about 0.01% to about 10%, preferably about 0.01% to about 1%, more preferably about 0.01% to about 0.5%, even more preferably about 0.01% to about 0.2%.

In certain embodiments, the effective amount of the agent is in the range of about 1% to about 5%, about 5% to about 10%, about 10% to about 15%, about 15% to about 20%, about 20% to about 25%, about 25% to about 30%, about 30% to about 35%, about 35% to about 40%, about 40% to about 45% or about 45% to about 50%.

Solid solutes, present initially in excess, can be in any suitable physical form such as particles, crystals, pellets, tablets, strips, film; granules and the like.

In certain embodiments, the pharmaceutical compositions of the invention comprise combinations of one or more active agents and an effective amount of another agent(s), such as a vasoconstrictor, tear substitute, antiallergenic agent, antihistamine, mast cell stabilizer, NSAID, steroid, anti-inflammatory, anti-oxidant, anti-infective, etc. The combinations of agents may act synergistically to decrease eyelid swelling.

Exemplary vasoconstrictors include, but are not limited to, naphazoline, antolazine, tetrahydrozoline, oxymetazoline and phenylephrine. Vasoconstrictors may additionally act as decongestants, in addition to reducing eyelid swelling. In certain embodiments, the effective amount of vasoconstrictor is in the range of about 0.01% to about 10%, preferably about 0.01% to about 1%, more preferably about 0.01% to about 0.5%, even more preferably about 0.01% to about 0.2%.

A variety of tear substitutes are known in the art and could be used in the compositions of the invention, including but not limited to: polyols such as, glycerol, glycerin, polyethylene glycol 300, polyethylene glycol 400, polysorbate 80, propylene glycol, and ethylene glycol, polyvinyl alcohol, povidone, and polyvinylpyrrolidone; cellulose derivatives such hydroxypropyl methylcellulose (also known as hypromellose), carboxy methylcellulose sodium, hydroxypropyl cellulose, hydroxyethyl cellulose, and methylcellulose; dextrans such as dextran 70; water soluble proteins such as gelatin; carbomers such as carbomer 934P, carbomer 941, carbomer 940 and carbomer 974P; and gums such as HP-guar. Many such tear substitutes are commercially available, which include, but are not limited to cellulose esters such as Bion Tears®, Celluvisc®, Genteal®, OccuCoat®, Refresh®, Teargen II®, Tears Naturale®, Tears Naturale 118®, Tears Naturale Free®, and TheraTears®; and polyvinyl alcohols such as Akwa Tears®, HypoTears®, Moisture Eyes®, Murine Lubricating®, and Visine Tears®. In other embodiments, the tear substitute is that which is described in U.S. Pat. No. 6,806,364, which is expressly incorporated by reference herein in its entirety. The formulation described in U.S. Pat. No. 6,806,364 contains 0.2 to 2.5 (e.g., 0.5 to 0.8) percent by weight of hydroxypropyl methylcellulose, 0.045 to 0.065 (e.g., 0.05 to 0.06) percent by weight a calcium salt, and 0.14 to 1.4 (e.g., 0.3 to 1.2) percent by weight a phosphate salt. AST has a viscosity of 20 to 150 (e.g., 50 to 90) centipoise and is buffered to a pH 5.5 to 8.5 (e.g., 6 to 8) with a phosphate salt or other suitable salts. It may further contain one or more of the following ingredients: 0.5 to 1.0 percent by weight glycerol, 0.5 to 1.0 percent by weight propyleneglycerol, 005 to 0.05 percent by weight glycine, 0.006 to 0.08 percent by weight sodium borate, 0.025 to 0.10 percent by weight magnesium chloride, and 0.001 to 0.01 percent by weight zinc chloride.

Tear substitutes may also be comprised of paraffins, such as the commercially available Lacri-Lube® ointments. Other commercially available ointments that are used as tear substitutes include Lubrifresh PM®, Moisture Eyes PM® and Refresh PM®.

Exemplary NSAIDs suitable for use in the compositions of the invention include but are not limited to, amfenac, propionic acids such as naproxen, flurbiprofen, oxaprozin, ibuprofen, ketoprofen, fenoprofen; ketorolac tromethamine (Acular®) (and the other compounds described as being opthalmologically effective in U.S. Pat. No. 4,454,151 to Waterbury, issued Jun. 12, 1984, the pertinent portions of which are incorporated herein by reference); acetic acid derivatives such as sulindac, indomethacin, and etodolac; phenylacetic acids such as diclofenac (Voltaren®) (and the other compounds described as being opthalmologically effective in U.S. Pat. No. 4,960,799 to Nagy, issued Oct. 2, 1990, the pertinent portions of which are incorporated herein by reference), bromfenac, and suprofen; arylacetic prodrugs such as nepafenac; salicyclic acids, such as aspirin, salsalate, diflunisal, choline magnesium trisalicylate (CMT); para-aminophenol derivatives such as acetaminophen; naphthylalkanones such as nabumetone; enolic acid derivatives such as piroxicam and meloxicam; femanates such as mefenamic acid, meclofenamate and flufenamic acid; pyrroleacetic acids such as tolmetin; and pyrazolones such as phenylbutazone; COX-2 selective inhibitors such as celecoxib, valdecoxib, parecoxib, etoricoxib, and luaricoxib; including all esters and pharmaceutically acceptable salts thereof.

Exemplary antihistamines include, but are not limited to, pheniramine, antazoline, emedastine difumarate, ebastine, carebastine, and levocabastine.

Exemplary mast cell stabilizers include, but are not limited to, nedocromil, lodoxamide, pemirolast, cromolyn, and cromolyn sodium.

Exemplary drugs with multiple modes of action include, but are not limited to, azelastine, epinastine, olopatadine, ketotifen fumarate, bilastine, bepotastine, and mizolastine.

The one or more active agents of the pharmaceutical compositions may be in the form of a pharmaceutically acceptable salt.

The pharmaceutical compositions may be formulated for topical administration as solutions, suspensions, oils, viscous or semi-viscous gels, emulsions, liposomes, lotions, ointments, creams, gels, salves, powders, and sustained or slow release, as well as eyelid lotion, or other types of solid or semi-solid compositions, including formulations described in U.S. Pat. No. 6,806,364. The composition may also be topically administered in a sprayable form.

Preferably, the pharmaceutical compositions are gels for controlled- or sustained-release of one or more pharmaceutically active agents (e.g., an osmotically active agent or vasoconstrictor, or a combination thereof). The formulation may be an in situ gellable aqueous formulation. Such a formulation comprises a gelling agent in a concentration effective to promote gelling upon contact with the eye or with lacrimal fluid in the exterior of the eye. Suitable gelling agents include, but are not limited to, thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

The phrase "in situ gellable" as used herein embraces not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye. Although it is preferred that such a formulation exhibit further increase in viscosity or gel stiffness upon administration, this is not absolutely required if the initial gel is sufficiently resistant to dissipation by lacrimal drainage to provide the effective residence time specified herein.

Sustained release ophthalmic formulations of highly viscous gels have been described in U.S. Pat. Nos. 4,271,143 and 4,407,792. Further, U.K. Patent Application GB 2007091 A, describes an ophthalmic composition in the form of a gel comprising an aqueous solution of a carboxyvinyl polymer, a water-soluble basic substance and an ophthalmic drug. Alternatively, U.S. Pat. No. 4,615,697, discloses a controlled release composition and method of use based on a bioadhesive and a treating agent.

In certain embodiments, the pharmaceutical compositions according to the present invention may be formulated as hyperosmotic solutions for topical administration. Aqueous solutions are easy to formulate, and are easily administered by a patient by means of instilling one to two drops of the solutions in the affected eyes.

Any of a variety of carriers may be used in the formulations of the present invention including water, mixtures of water and water-miscible solvents, such as, but not limited to, C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100,000 times the concentration of the active ingredient.

Additional ingredients that may be included in the formulation include tonicity enhancers, preservatives, solubilizers, non-toxic excipients, demulcents, sequestering agents, pH adjusting agents, co-solvents and viscosity building agents.

For the adjustment of the pH, preferably to a physiological pH, buffers may be especially useful. The pH of the present solutions should be maintained within the range of 4.0 to 8.0, more preferably about 4.0 to 6.0, more preferably about 6.5 to 7.8. Suitable buffers may be added, such as, but not limited to, boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Generally, buffers will be used in amounts ranging from about 0.05 to 2.5 percent by weight, and preferably, from 0.1 to 1.5 percent.

Tonicity is adjusted if needed typically by tonicity enhancing agents. Such agents may, for example be of ionic and/or non-ionic type. Examples of ionic tonicity enhancers are, but are not limited to, alkali metal or earth metal halides, such as, for example, $CaCl_2$, KBr, KCl, LiCl, NaI, NaBr or NaCl, $Na_2SO4$ or boric acid. Non-ionic tonicity enhancing agents are, for example, urea, glycerol, sorbitol, mannitol, propylene glycol, or dextrose. These agents may also serve as the active agents in certain embodiments. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

In certain embodiments, the topical formulations additionally comprise a preservative. A preservative may typically be selected from a quaternary ammonium compound such as benzalkonium chloride (N-benzyl-N—($C_8$-$C_{18}$ alkyl)-N,N-dimethylammonium chloride), benzoxonium chloride or the like. Examples of preservatives different from quaternary ammonium salts are alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, Germal® II or sorbic acid. Preferred preservatives are quaternary ammonium compounds, in particular benzalkonium chloride or its derivative such as Polyquad (see U.S. Pat. No. 4,407,791), alkyl-mercury salts and parabens. Where appropriate, a sufficient amount of preservative is added to the ophthalmic composition to ensure protection against secondary contaminations during use caused by bacteria and fungi.

In another embodiment, the topical formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

The topical formulation may additionally require the presence of a solubilizer, in particular if the active or the inactive ingredients tends to form a suspension or an emulsion. A solubilizer suitable for an above concerned composition is for example selected from the group consisting of tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of those compounds. A specific example of an especially preferred solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. Another preferred solubilizer is selected from tyloxapol and from a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

The formulations may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight.

Other compounds may also be added to the formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

4. Methods of Use

The invention features methods of treating and preventing eyelid swelling in a subject comprising use of the novel formulations described above. For example, a method of treating eyelid swelling comprises administering to the eye surface of the subject a pharmaceutical composition comprising an effective amount of an osmotically active agent and/or vasoconstrictor and/or astringent in a pharmaceutically acceptable carrier. As another example, a method of treating eyelid swelling may comprise administering the outer and/or inner eyelid surface of the subject a pharmaceutical composition comprising an effective amount of an osmotically active agent and/or vasoconstrictor and/or astringent in a pharmaceutically acceptable carrier. Various embodiments of such formulation are described above. In various embodiments, the composition may be administered in the form of an emulsion or suspension, liposome, lotion, ointment, cream, gel, salve, or powder, and sustained or slow release, as well as eyelid lotions, or other types of solid or semi-solid compositions, including formulations described in U.S. Pat. No. 6,806,364. It may also be used as an eye wash or rinse to irrigate the eye. The composition may also be administered in a sprayable form.

The effective amount of osmotically active agent and/or vasoconstrictor and/or astringent in the formulation will depend on absorption, inactivation, and excretion rates of the drug and the delivery rate of the compound from the formulation. In certain embodiments comprising an osmotically active agent, the effective amount will also depend on the concentration of agent required to make the formulation a hyperosmotic solution. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of any compound of the present invention will vary depending on the symptoms, age and other physical characteristics of the patient, the nature and severity of the disorder to be treated or prevented, the degree of comfort desired, the route of administration, and the form of the supplement. Any of the subject formulations may be administered in a single dose or in divided doses. Dosages for the formulations of the present invention may be readily determined by techniques known to those of skill in the art or as taught herein.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the agent and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several agents formulated into the compositions of the present invention may reduce the required dosage for any individual component because the onset and duration of effect of the different components may be complimentary. In such combined therapy, the different agents may be delivered together or separately, and simultaneously or at different times within the day.

Efficacy of the formulations and compositions of the invention in treating and preventing eyelid swelling may be assessed by measuring changes in eyelid swelling, using various methods, including but not limited to ruler measurements, subjective scales (for example, but not limited to, subjective clinical scales that determine swelling as mild, moderate, severe, or 0, 1, 2, or 3, or other appropriate scale), and scanning technology. In a preferred embodiment, changes in eyelid swelling are assessed using 3D scanning technology. Use of 3D scanning technology enables the quantification of the daily fluctuation in lid swelling, which has not been accurately measured previously, to assess the reduction of lid swelling using various formulations of the invention.

5. Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP"), other publications by the Food and Drug Administration, and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.
6. Kits In still another embodiment, this invention provides kits for the packaging and/or storage and/or use of the formulations described herein, as well as kits for the practice of the methods described herein. Thus, for example, kits may comprise one or more containers containing one or more ophthalmic preparations, tablets, or capsules of this invention. The kits can be designed to facilitate one or more aspects of shipping, use, and storage.

The kits may optionally include instructional materials containing directions (i.e., protocols) disclosing means of use of the formulations provided therein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to interne sites that provide such instructional materials.

EXAMPLES

The invention, having been generally described, may be more readily understood by reference to the following examples, which are included merely for purposes of illustration of certain aspects and embodiments of the present invention, and are not intended to limit the invention in any way.

Example 1

Figure 3A:
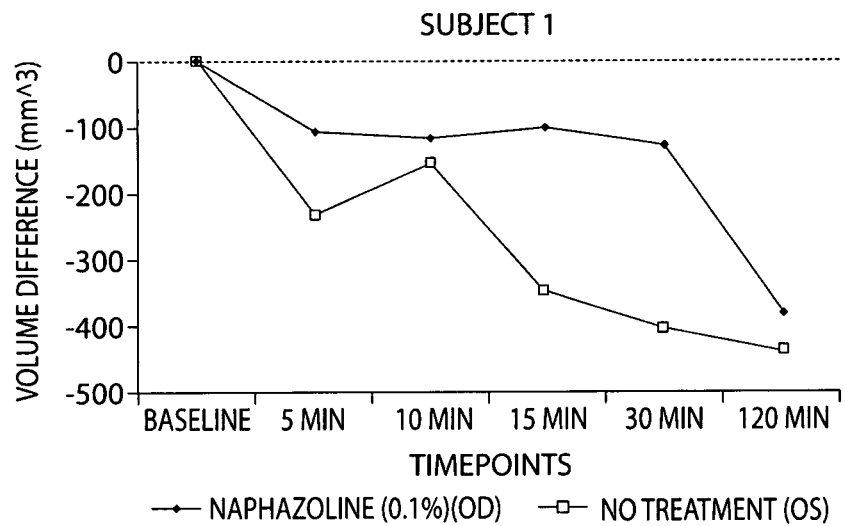
FIGS. 3A-3L are line graphs depicting the results of a study using naphazoline 0.1% for treatment of morning lid swelling in 11 subjects. In each of FIGS. 3A-3L, values are represented with respect to baseline, timepoints represents time after instillation of the study drug. For each subject, the right eye (circle) was treated with naphazoline hydrochloride (0.1%) while the left eye (square) received no treatment.
Figure 3B:
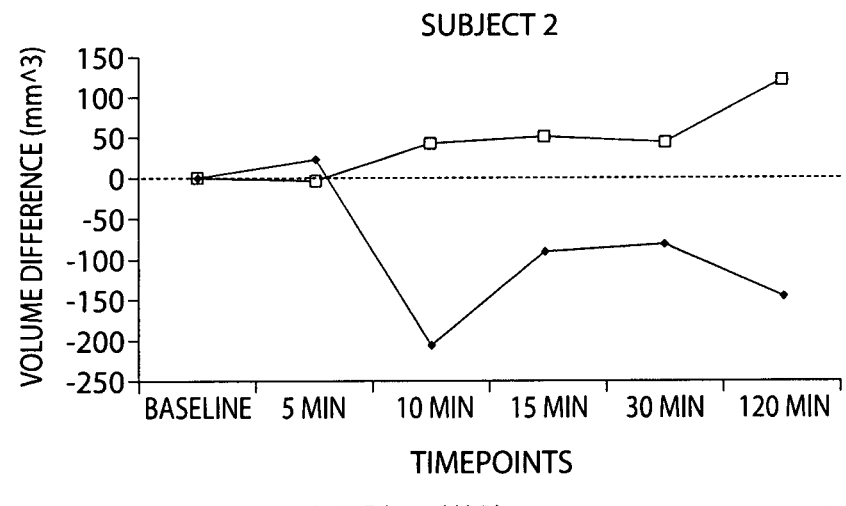
Figure 3C:
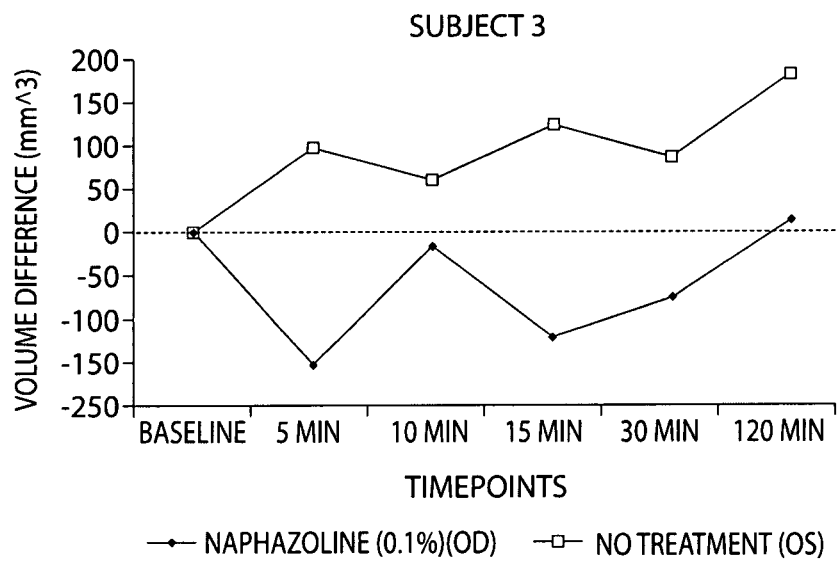
Figure 3D:
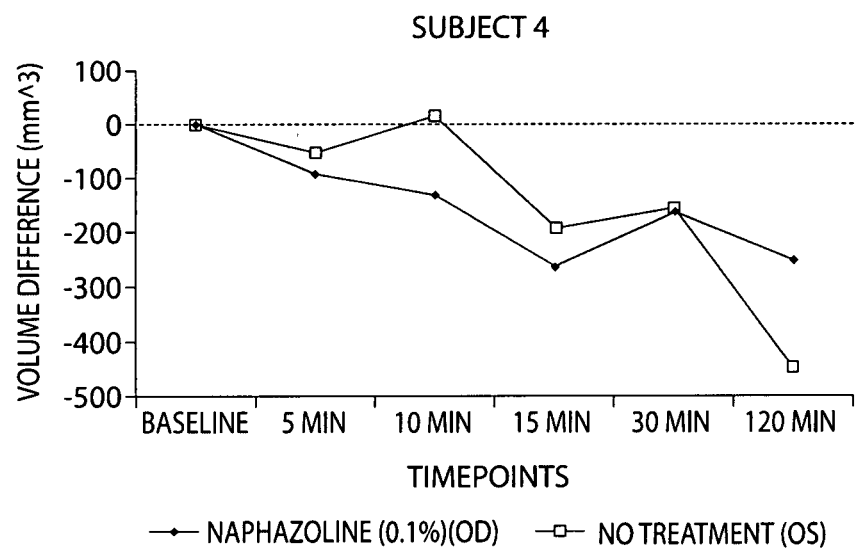
Figure 3E:
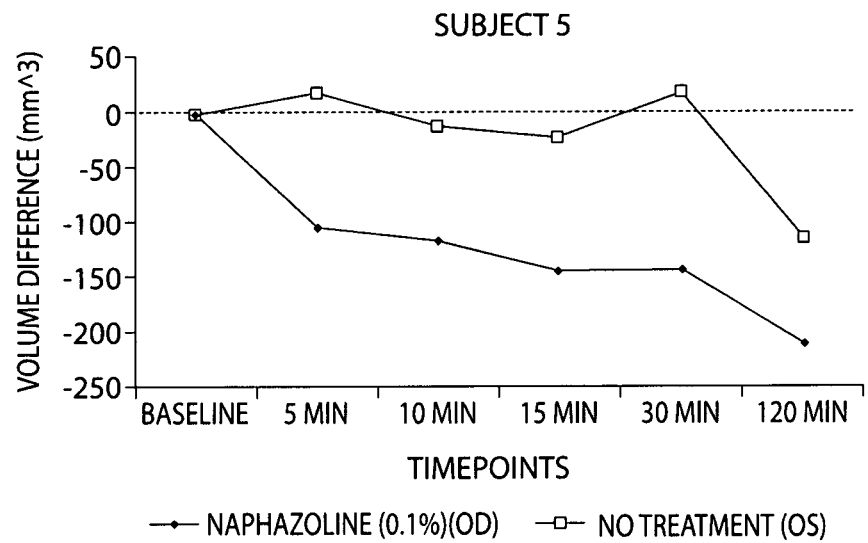
Figure 3F:
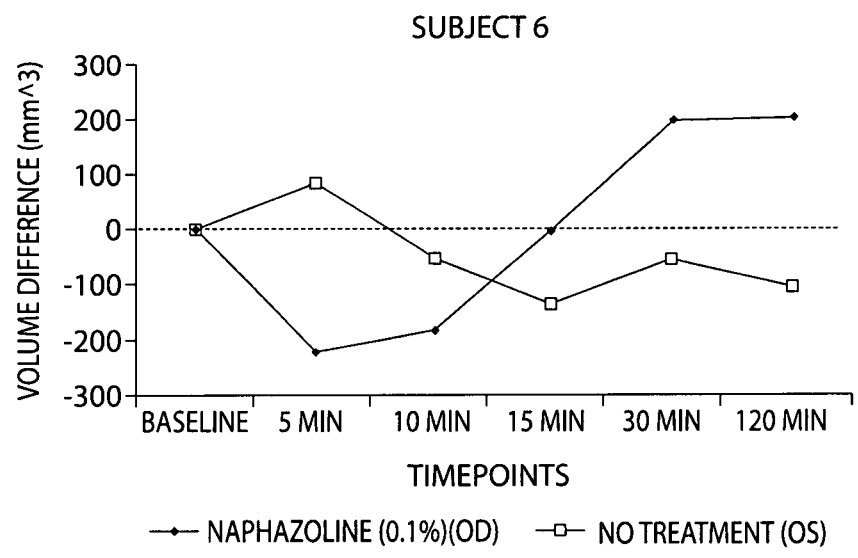
Figure 3G:
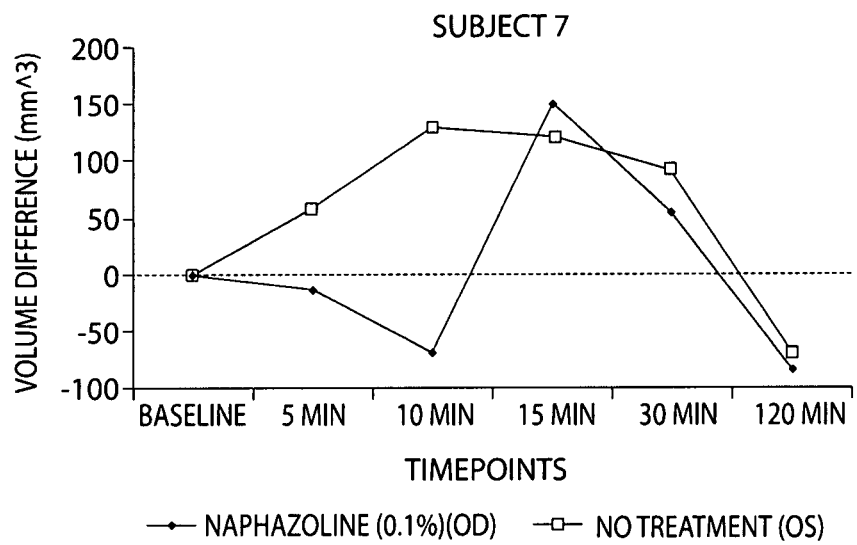
Figure 3H:
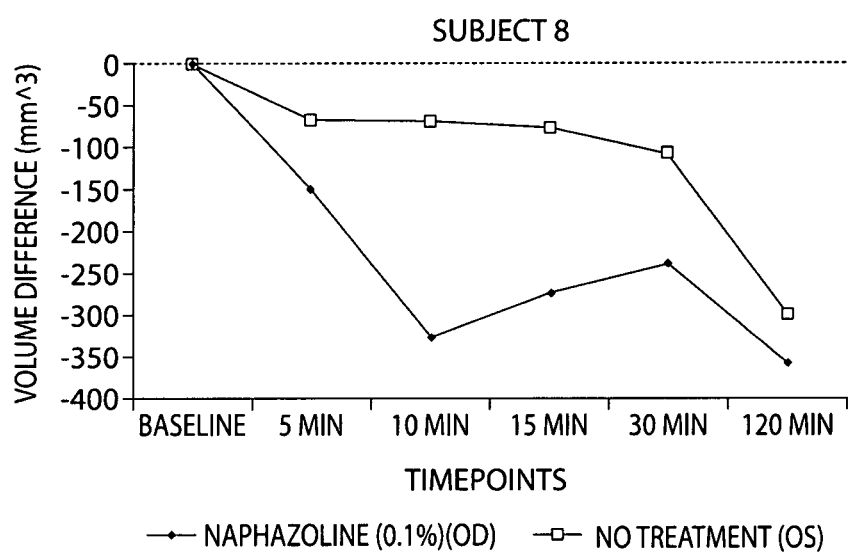
Figure 3I:
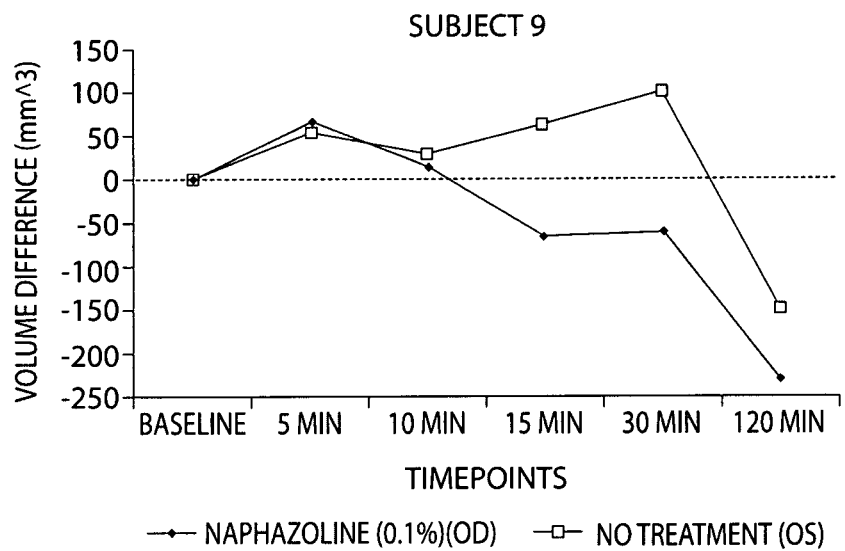
Figure 3J:
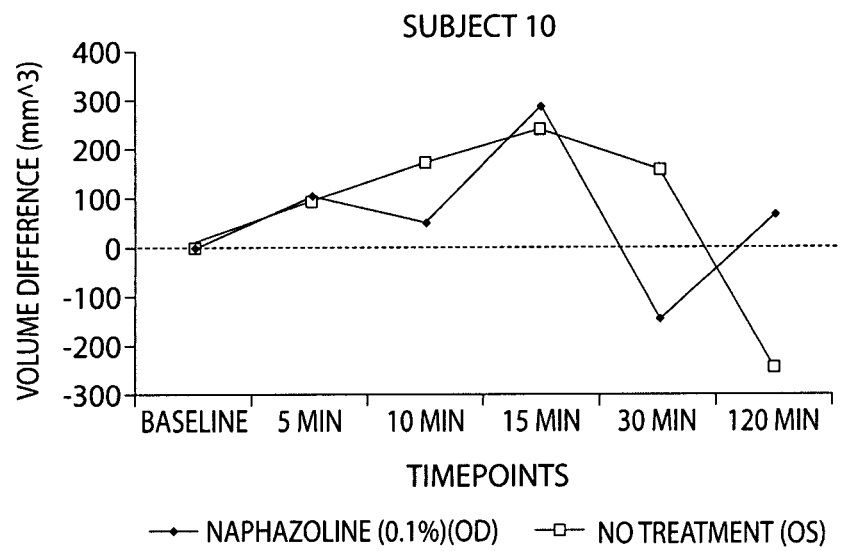
Figure 3K:
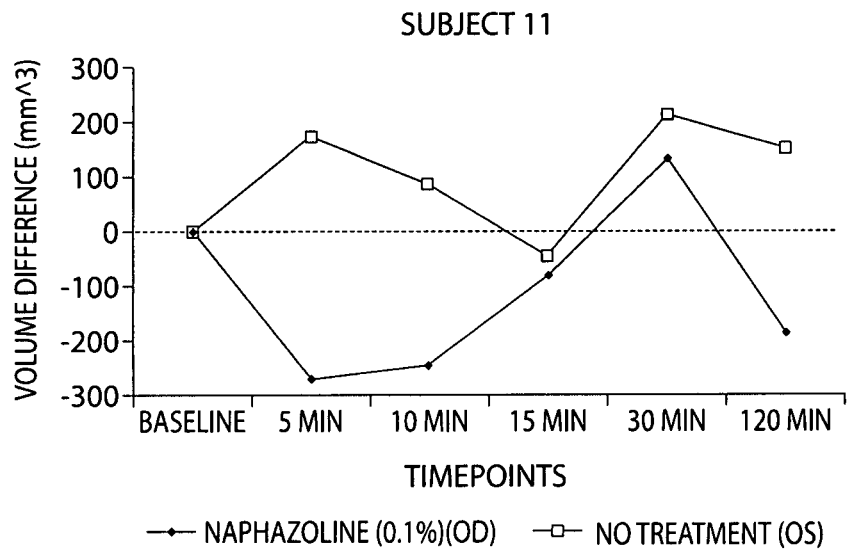
Figure 3L:
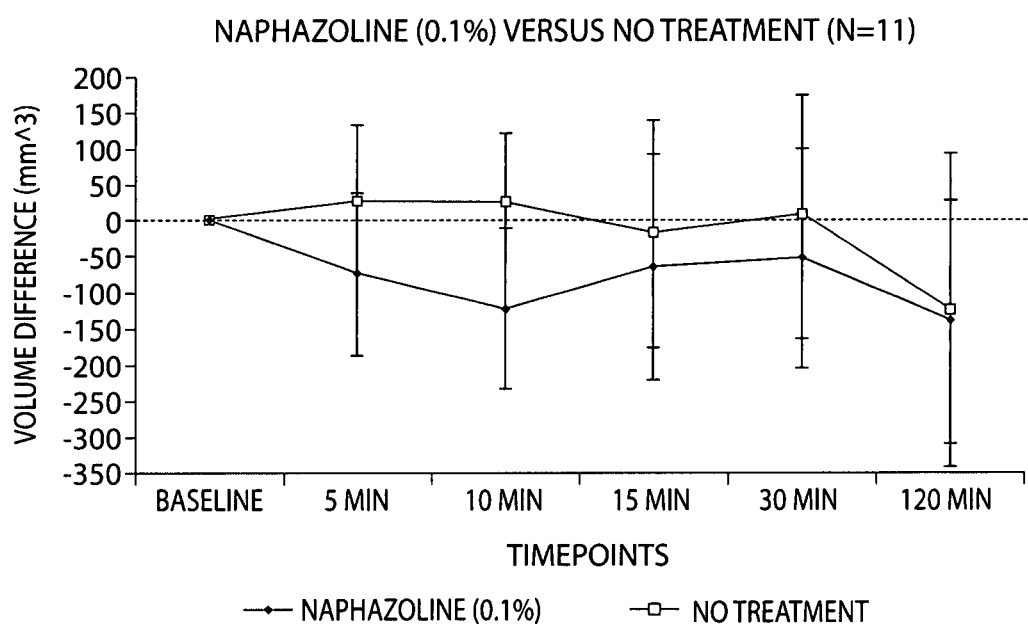
Figure 4A:
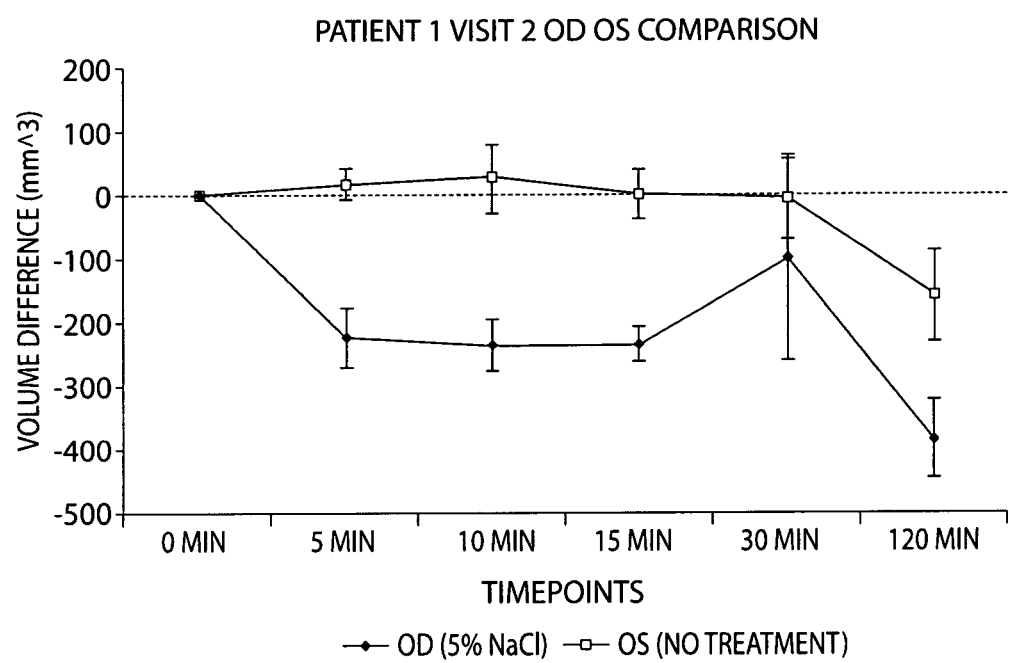
FIGS. 4A-4G are line graphs depicting the results of a study evaluating NaCl 5% ophthalmic solution for treatment of morning eyelid edema in 6 subjects. In each of FIGS. 4A-4G, values are represented with respect to baseline, error bar represents one standard error, and timepoints represents time after instillation of the study drug. For each subject, no treatment was administered in either eye at baseline, the right eye (circle) was treated with NaCl 5% ophthalmic solution while the left eye (square) received no treatment.
Figure 4B:
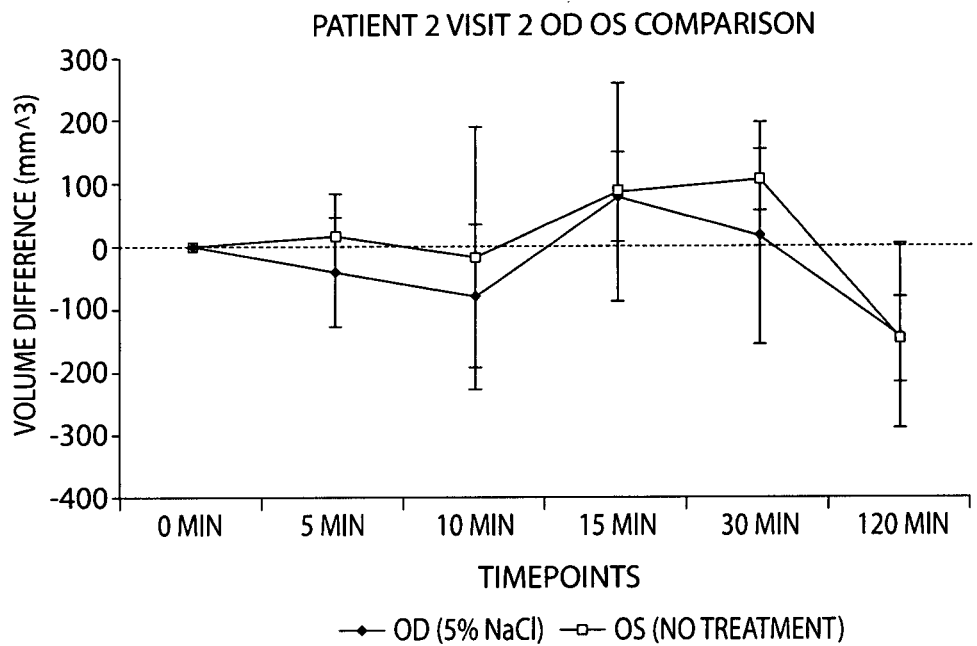
Figure 4C:
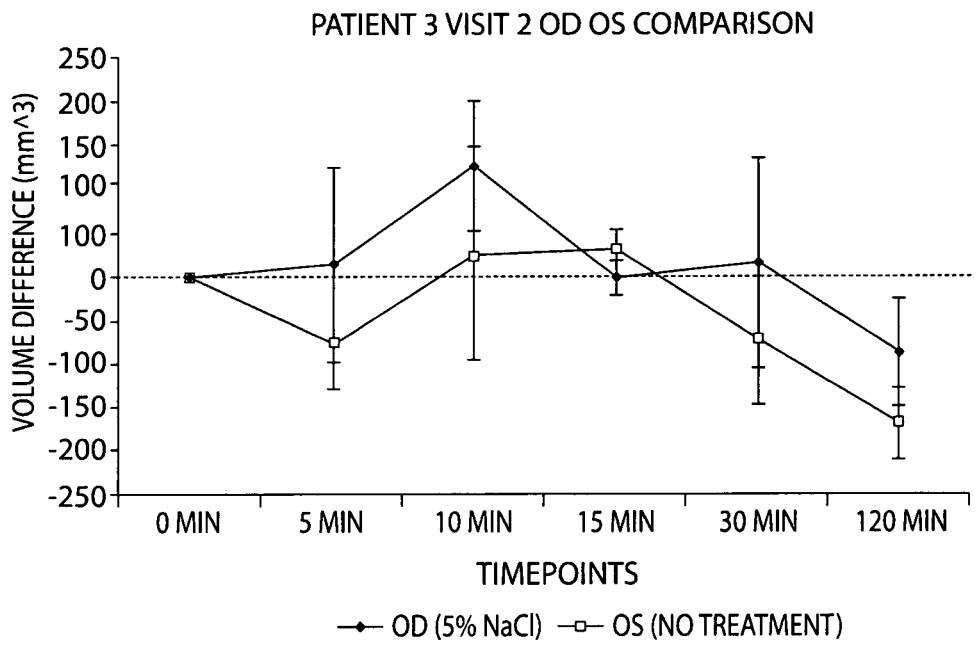
Figure 4D:
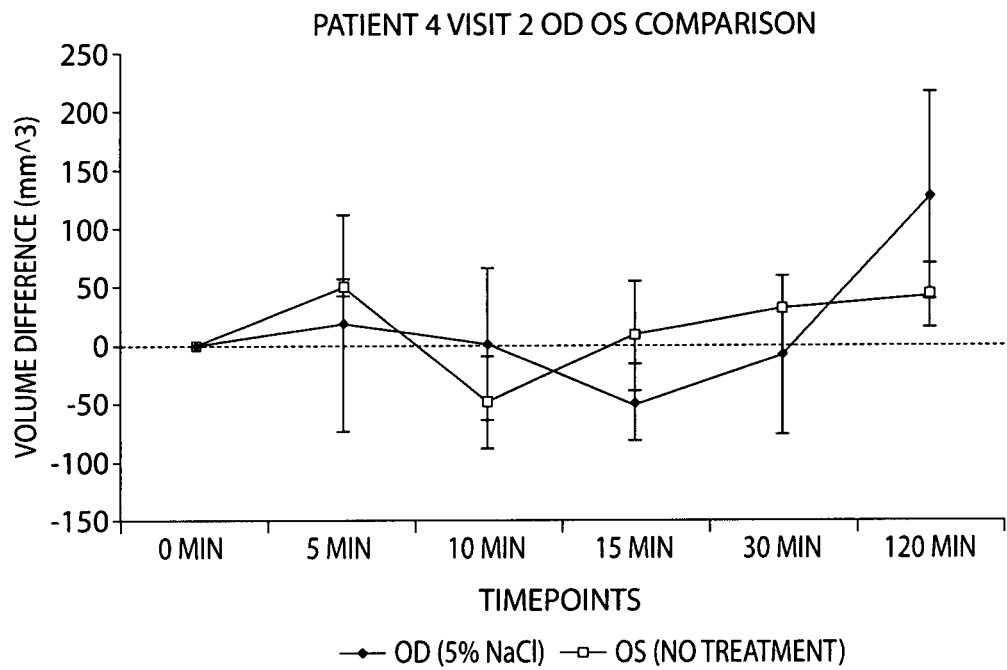
Figure 4E:
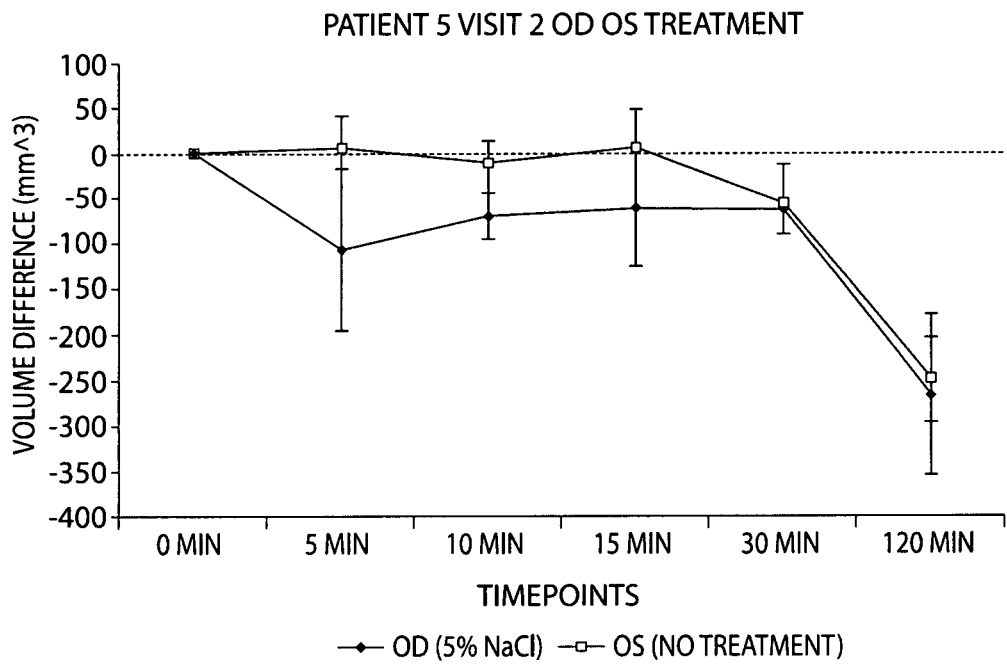
Figure 4F:
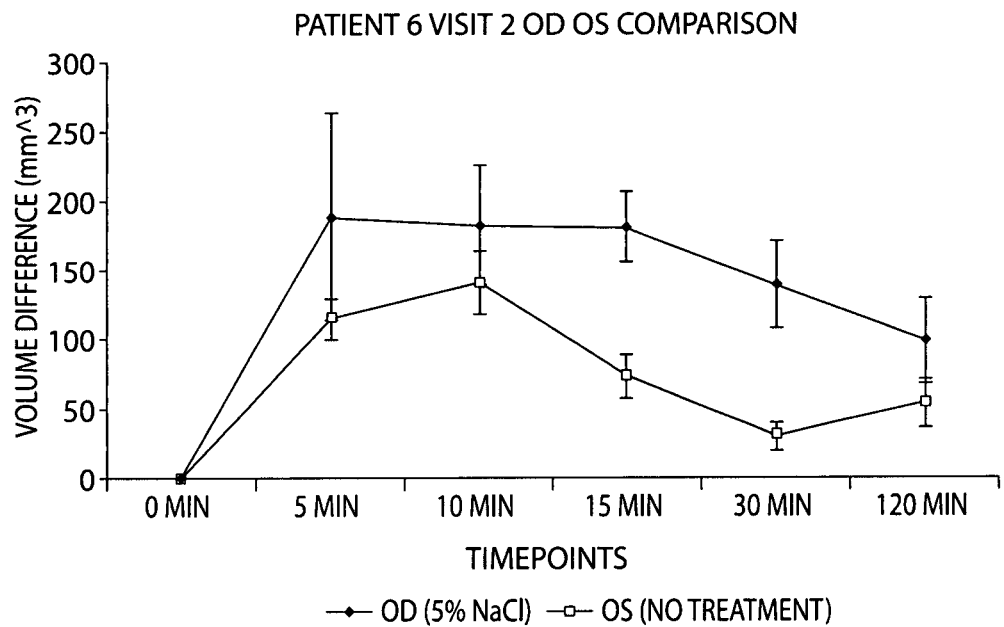
Figure 4G:
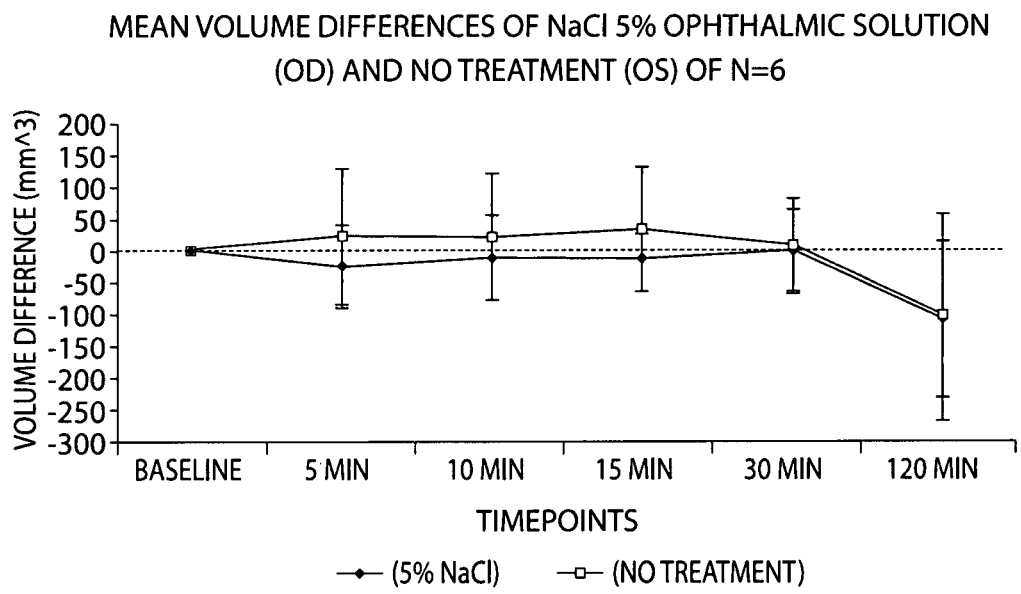

Use of Naphazoline 0.1% Ophthalmic Solution as a Treatment for Morning Eyelid Edema In this study, the efficacy of naphazoline 0.1% ophthalmic solution was evaluated for treatment for eyelid edema. The eyelid volume for 11 subjects participating in the study was recorded in the afternoon of Day 1 and again upon arrival to the clinic the following morning (Day 2). All subjects showed an increase in eyelid swelling at the morning scan during Visit 2. The natural progression of morning eyelid swelling, as measured using 3D scanning technology is depicted in FIG. 10. The increase ranged from 14 mm$^3$ to 659 mm$^3$. Subjects were then dosed with naphazoline 0.1% (vasoconstrictor) in the right eye and eyelid volume was assessed at 5, 10, 15, 30, and 120 minutes following treatment using a 3-D scanner. As shown in FIG. 3, two drops of naphazoline 0.5% solution caused a reduction of eyelid swelling in most subjects. 9 out of 11 subjects showed greater decrease in volume in the treatment eye (naphazoline 0.1%) than the non-treatment eye up to the 30 minute timepoint (FIGS. 3B-E, G-K). Up to the 120 minute timepoint, 7 out of 11 subjects showed greater decrease in volume in the right eye than the left eye (FIGS. 3B, C, E, G-I, K). A summary of all the patient data is depicted if FIG. 3L.

Overall, these results demonstrated efficacy of the naphazoline 0.1% for ability to reduce eyelid swelling in patients with morning lid swelling and not in a diseased eye or eye with current vasodilation where a vasoconstrictor would be typically used.

Example 2

Use of a Colloidal Osmotic Agent, NaCl 5% Ophthalmic Solution, for Treatment of Morning Eyelid Edema In a preliminary study with a similar design to that described above, NaCl 5% ophthalmic solution was evaluated as a potential treatment for eyelid edema. Two drops of medication were applied topically and caused a reduction of eyelid swelling in several patients (FIG. 4). Eyelid swelling was assessed using a 3-D scanner at 5, 10, 15, 20, 30, and 120 minutes post-treatment. Three patients demonstrated a reduction in eyelid swelling through 15 minutes post-instillation. In one subject, this reduction was pronounced and was present through the 120 minute assessment time point. In the remaining three patients, treatment was not effective.

Overall, these results demonstrated some efficacy of the NaCl 5% for ability to reduce eyelid swelling in certain patients. An assessment of mean change from baseline (FIG. 4G) suggests that NaCl treatments were numerically superior to negative controls, though the differences were not statistically significant in this small study.

Further, naphazoline 0.1% in combination with 5% NaCl demonstrates superior efficacy in reducing eyelid swelling in patients as compared to the individual components (FIGS. 5 and 6).

Example 3

Use of Naphazoline 0.05%/5% NaCl Ointment for Treatment of Morning Eyelid Edema

The efficacy of Naphazoline hydrochloride (0.05%) dissolved in 5% NaCl ophthalmic ointment in preventing morning eyelid swelling was evaluated in four (4) patients. Three dimensional scans were taken of each patient and each eye during the afternoon between 4:30 to 5:30 pm. Each patient was asked to take home a vial containing 5% NaCl ophthalmic ointment containing naphazoline hydrochloride (0.05%) and apply the ointment into the conjunctival sac of the right eye immediately prior to sleep. The following morning, between 7:30 to 8:00 am, patients were scanned again for each eye. The mean volumes of the upper and lower eyelid regions were calculated for both afternoon and morning scans of each patient. The differences between the means were also calculated. Results showed that the treatment eye had approximately half the swelling of the untreated eye (FIG. 7).

The final formulation used in this study was: sodium chloride (5%) in lanolin, mineral oil, purified water, white petrolatum, and naphazoline hydrochloride (0.05%).

Example 4

Use of Sodium Chloride (2.5%) and Naphazoline (0.1%) for the Treatment of Morning Eyelid Edema The efficacy of Naphazoline (0.1%) in combination with sodium chloride (2.5%) solution in treating and/or preventing morning eyelid swelling was evaluated, as measured by 3D scanning technology.

Sodium chloride (2.5%) was formulated with water. Naphazoline was then dissolved in NaCl (2.5%) solution to formulate naphazoline (0.1%) concentration.

A total of 6 subjects (male, between the ages of 25 and 29) were evaluated. At the start of the study, five (5) baseline scans were performed per subject and eye using a 3D scanner. The next day, subjects were asked to five (5) scans of each eye, identical to Visit 1, were then taken.

Subjects received the 2 drops (40 μl each) of the combination treatment, with one minute apart each drop in one eye and no treatment in the other eye. Five (5) scans of each eye were taken, identical to Visit 1, 20 minutes after second drop instillation. Subjects were asked to grade their eyelid swelling post treatment. Digital photos were also taken at baseline and at 20 minutes post treatment.

The mean comfort level immediately after instillation was 3.3. Mean eyelid volume increase in the morning was 243 and 309 mm$^3$ for the right eye and left eye, respectively. The mean decrease 20 minutes after treatment was −100 and −14 mm$^3$ for the treatment eye and no treatment eye, respectively.

These results suggest that the 2.5% NaCl did reduce morning eyelid swelling (FIG. 8). In comparison with 5% NaCl in combination with 0.1% naphazoline, 2.5% NaCl was less efficacious (approximately by half) (See FIGS. 6 and 8). This suggests that the efficacy of NaCl in treating morning eyelid swelling is directly related to concentration.

In terms of comfort level, the 2.5% was more comfortable than the 5% NaCl, which is an improvement. The mean comfort level for this study (3.3) was more comfortable than the 5% NaCl/0.1% naphazoline combination (5.8).

Example 5

Use of Sucrose 50% and Naphazoline (0.1%) for the Treatment of Morning Eyelid Edema The efficacy of Naphazoline (0.1%) in combination with sucrose 50% solution in treating and/or preventing morning eyelid swelling was evaluated, as measured by 3D scanning technology.

Sucrose was formulated with water. Naphazoline was then dissolved in the sucrose solution to formulate naphazoline (0.1%) concentration.

A total of 6 subjects were evaluated and methods were similar to previous experiments. At the start of the study, five (5) baseline scans were performed per subject and eye using a 3D scanner. The next day, subjects were asked to five (5) scans of each eye, identical to Visit 1, were then taken.

Subjects received the 2 drops (40 μl each) of the combination treatment, with one minute apart each drop in one eye and no treatment in the other eye. Five (5) scans of each eye were taken, identical to Visit 1, 20 minutes after second drop instillation. Subjects were asked to grade their eyelid swelling post treatment. Digital photos were also taken at baseline and at 20 minutes post treatment.

These results suggest that the 50% sucrose/0.1% naphazoline formulation did reduce morning eyelid swelling (FIG. 9).

Example 6

Use of Phenylephrine 0.25% Ointment for the Treatment of Morning Eyelid Edema

The efficacy of phenylephrine 0.25% ointment treating and/or preventing morning eyelid swelling was evaluated, as measured by 3D scanning technology.

A total of 6 subjects were evaluated and methods were similar to previous experiments. At the start of the study, five (5) baseline scans were performed per subject and eye using a 3D scanner. The next day, subjects were asked to five (5) scans of each eye, identical to Visit 1, were then taken.

Subjects received the 2 drops (40 μl each) of the combination treatment, with one minute apart each drop in one eye and no treatment in the other eye. Five (5) scans of each eye were taken, identical to Visit 1, 20 minutes after second drop instillation. Subjects were asked to grade their eyelid swelling post treatment. Digital photos were also taken at baseline and at 20 minutes post treatment.

These results suggest that the 0.25% phenylephrine formulation did reduce morning eyelid swelling (FIG. 11).

Example 7

Use of Mannitol 12.5% with 0.1% Naphazoline and 5% NaCl Solution for the Treatment of Morning Eyelid Edema The efficacy of mannitol 12.5% with 0.1% naphazoline in 5% NaCl solution for treating and/or preventing morning eyelid swelling was evaluated, as measured by 3D scanning technology.

A total of 6 subjects were evaluated and methods were similar to previous experiments. At the start of the study, five (5) baseline scans were performed per subject and eye using a 3D scanner. The next day, subjects were asked to five (5) scans of each eye, identical to Visit 1, were then taken.

Subjects received the 2 drops (40 µl each) of the combination treatment, with one minute apart each drop in one eye and no treatment in the other eye. Five (5) scans of each eye were taken, identical to Visit 1, 20 minutes after second drop instillation. Subjects were asked to grade their eyelid swelling post treatment. Digital photos were also taken at baseline and at 20 minutes post treatment.

These results suggest that the mannitol/naphazoline/NaCl combination did reduce morning eyelid swelling (FIG. 12).

Example 8

Use of Mannitol 12.5% Solution for the Treatment of Morning Eyelid Edema

The efficacy of mannitol 12.5% solution for treating and/or preventing morning eyelid swelling was evaluated, as measured by 3D scanning technology.

A total of 6 subjects were evaluated and methods were similar to previous experiments. At the start of the study, five (5) baseline scans were performed per subject and eye using a 3D scanner. The next day, subjects were asked to five (5) scans of each eye, identical to Visit 1, were then taken.

Subjects received the 2 drops (40 µl each) of the combination treatment, with one minute apart each drop in one eye and no treatment in the other eye. Five (5) scans of each eye were taken, identical to Visit 1, 20 minutes after second drop instillation. Subjects were asked to grade their eyelid swelling post treatment. Digital photos were also taken at baseline and at 20 minutes post treatment.

These results suggest that the mannitol 12.5% solution did reduce morning eyelid swelling (FIG. 13).

EQUIVALENTS

The present invention provides in part topical ophthalmic formulations for use in treating eyelid swelling. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications and patents mentioned herein, including those items listed below, are hereby incorporated by reference in their entireties as if each individual publication or patent was specifically and individually indicated to be incorporated by reference. In case of conflict, the present application, including any definitions herein, will control.

Juniper E F, Guyatt G H, and Dolovich J. 1994. Assessment of quality of life in adolescents with allergic rhinoconjunctivitis: Development and testing of a questionnaire for clinical trials. J Allergy Clin Immunol. 93: 413-423.

Beltrani V S. 2001. Eyelid dermatitis. Curr Allergy Asthma Rep. 1: 380-388. [0113] Zide B M and Jelks G W. 1985. The eyelids. Chapter 3, pp. 21-32, in Surgical Anatomy of the Orbit. Raven, N.Y.

Wobig J. 1982. Eyelid anatomy. Chapter 7, pp. 78-87, in Cosmetic Oculoplastic Surgery, Putterman A M, ed. Grune & Stratton, New York.

Langley K E, Patrinely J R, Anderson R L, and Thiese S M. 1987. Unilateral blepharochalasis. Ophthalmic Surg. 18: 594-598.

American Society for Aesthetic Plastic Surgery (ASAPS). News release: Mar. 4, 2003. Available at: http://www.surgery.org/news releases/mar0303stats.html.

Kolker A E. 1970. Hyperosmotic solutions in glaucoma. Investigative Opthalmology. 9: 418-423.

Bielory L. 2000. Allergic and immunologic disorders of the eye. Part II: Ocular allergy. J Allergy Clin Immunol. 106: 1019-1032.

Carter B B. 1999. Eye swelling and pain: a Chinese herbal case study. www.pulsemed.org.

Greiner J V, Peace D G, Baird R S, and Allansmith M R. 1985. Effects of eye rubbing on the conjunctiva as a model of ocular inflammation. Am J Opthalmol. 100: 45-50.

Chen D M and Crosby D L. 1997. Periorbital edema as an initial presentation of rosacea. J Am Acad Dermatol. 37: 346-348.

Smith N H, Rados W T, Cohen F B, and Cinotti A A. 1977. Malignant lymphoma presenting as bilateral swelling of the eyelid. J Med Soc NJ. 74: 968-970. [0123] Jacobson D M. 2000. Dysthyroid orbitopathy. Semin Neurol. 20: 43-54.

Dupouy-Camet J, Kociecka W, Bruschi F, et al. 2002. Opinion on the diagnosis and treatment of human trichinellosis. Expert Opin Pharmacother. 3: 1117-1130.

We claim:

1. A method of treating eyelid swelling in a subject comprising: administering to the eye surface of the subject a composition consisting of an effective amount of an osmotically active agent and a vasoconstrictor as active agents, wherein the osmotically active agent is glycerine and wherein the vasoconstrictor is oxymetazoline, and one or more pharmaceutically acceptable carriers and/or excipients.

2. The method of claim 1, wherein the effective amount of glycerine is about 1% to about 10%, and the effective amount of oxymetazoline is about 0.01% to about 0.2%.

3. The method of claim 2, wherein the effective amount of glycerine is 7.5% and the effective amount of oxymetazoline is 0.05%.

* * * * *